(12) United States Patent
Radgowski et al.

(10) Patent No.: US 8,052,644 B2
(45) Date of Patent: Nov. 8, 2011

(54) SURGICAL IRRIGATION SYSTEM

(75) Inventors: Todd J. Radgowski, San Jose, CA (US);
Reid S. Cover, Mountain View, CA (US); Brannon P. Wells, San Jose, CA (US); Simon S. Hui, San Jose, CA (US)

(73) Assignee: Stryker Corporation, Kalamazoo, MI (US)

( * ) Notice: Subject to any disclaimer, the term of this patent is extended or adjusted under 35 U.S.C. 154(b) by 1363 days.

(21) Appl. No.: 11/639,360

(22) Filed: Dec. 14, 2006

(65) Prior Publication Data

US 2007/0233003 A1 Oct. 4, 2007

Related U.S. Application Data

(60) Provisional application No. 60/750,102, filed on Dec. 14, 2005.

(51) Int. Cl.
*A61M 1/00* (2006.01)
*A61M 31/00* (2006.01)
*A61M 37/00* (2006.01)

(52) U.S. Cl. .......... 604/151; 604/67; 604/118; 604/131; 604/500

(58) Field of Classification Search ............. 604/29–34, 604/122, 123, 131, 507, 67, 118, 151, 500; 417/477.2
See application file for complete search history.

(56) References Cited

U.S. PATENT DOCUMENTS

| 5,133,650 | A | * | 7/1992 | Sunderland et al. ....... 417/477.2 |
| 5,246,422 | A | | 9/1993 | Favre |
| 5,464,391 | A | | 11/1995 | DeVale |
| 5,484,402 | A | | 1/1996 | Saravia et al. |
| 5,620,312 | A | * | 4/1997 | Hyman et al. ................ 417/474 |
| 6,077,246 | A | | 6/2000 | Kullas et al. |
| 6,162,194 | A | | 12/2000 | Shipp |
| 6,213,970 | B1 | | 4/2001 | Nelson et al. |
| 6,358,224 | B1 | | 3/2002 | Tims et al. |
| 6,436,072 | B1 | | 8/2002 | Kullas et al. |
| 6,623,445 | B1 | | 9/2003 | Nelson et al. |
| 6,652,488 | B1 | | 11/2003 | Cover et al. |
| 2005/0095155 | A1 | | 5/2005 | Blight et al. |
| 2006/0285986 | A1 | | 12/2006 | Radgowski et al. |

* cited by examiner

*Primary Examiner* — Nicholas Lucchesi
*Assistant Examiner* — Nathan R Price
(74) *Attorney, Agent, or Firm* — Flynn, Thiel, Boutell & Tanis, P.C.

(57) ABSTRACT

This invention relates to a surgical irrigation system having an improved reusable, motorized console and a separable/attachable irrigation pump cassette, including, at least in one embodiment improved mechanical and electrical inner-connection structure therebetween, and at least in one embodiment improved pump priming structure and methods.

21 Claims, 34 Drawing Sheets

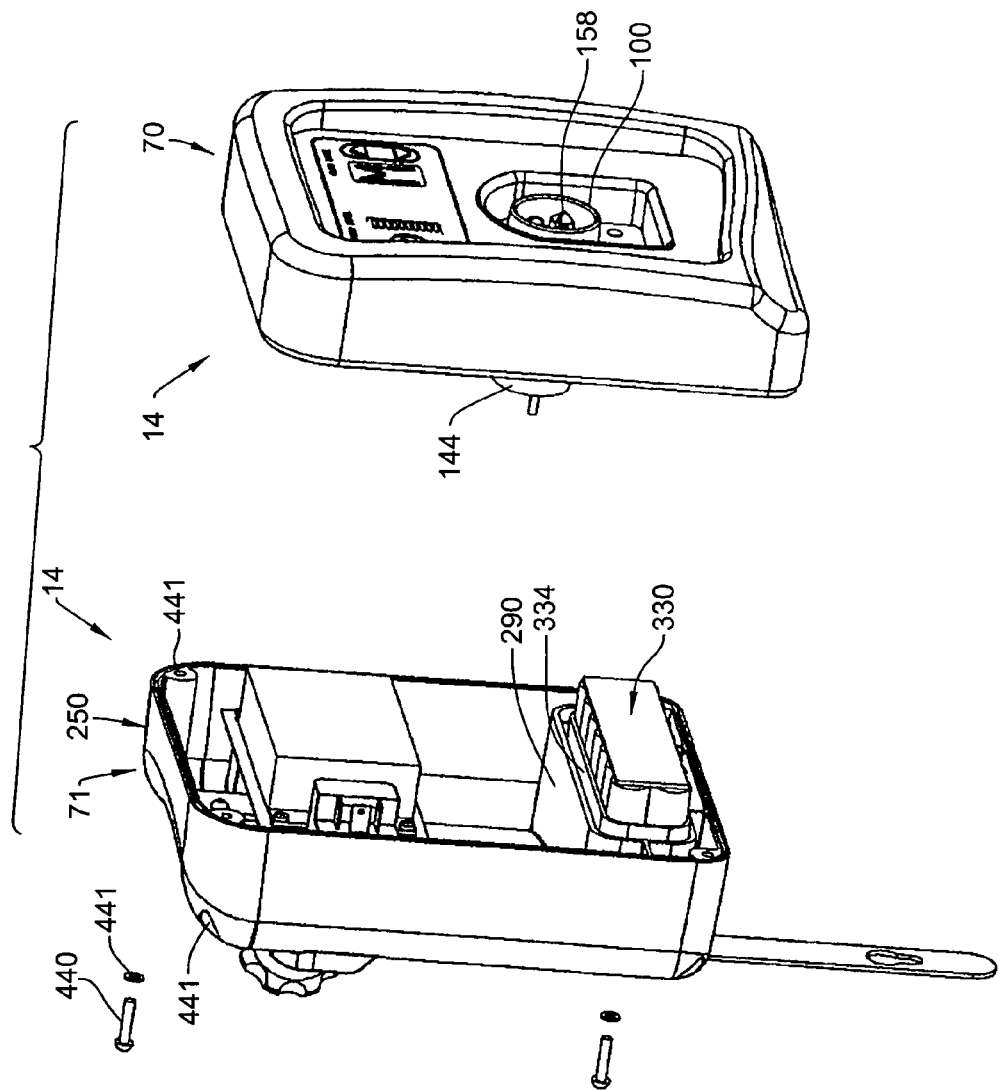

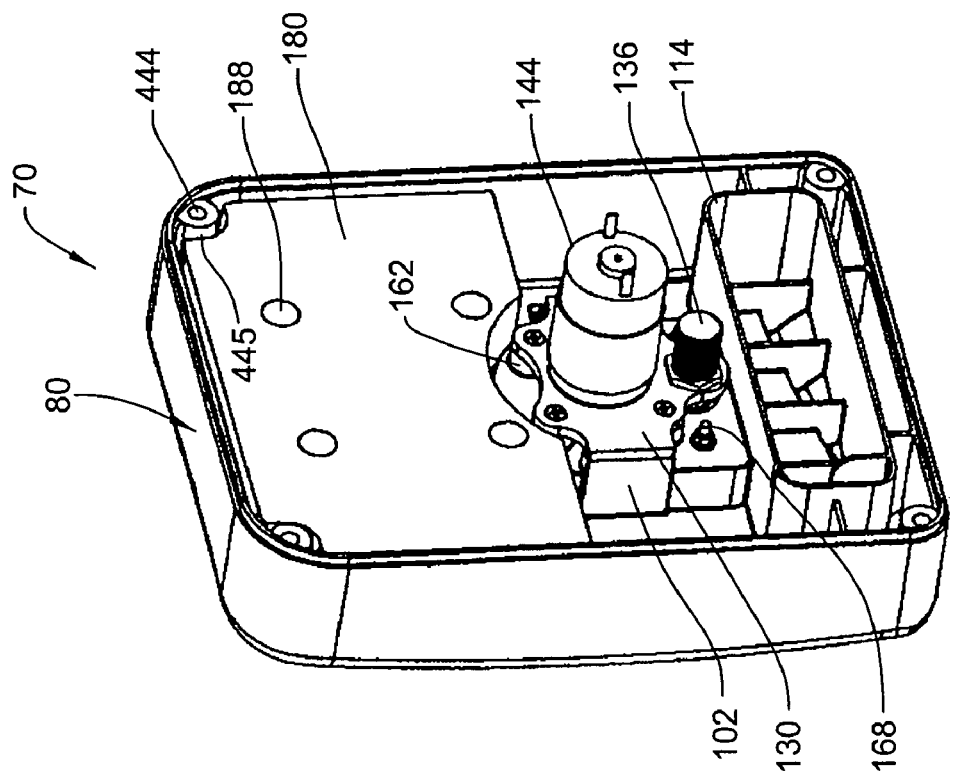
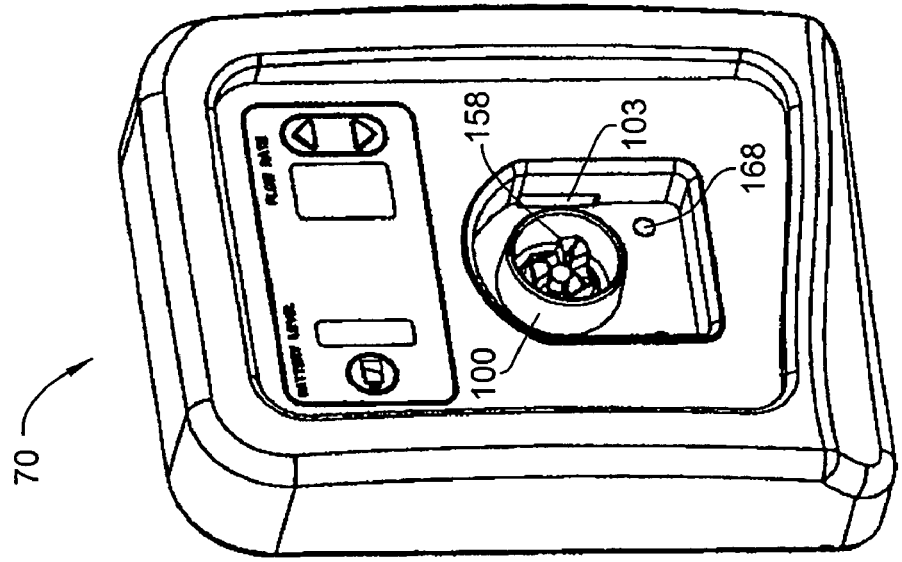

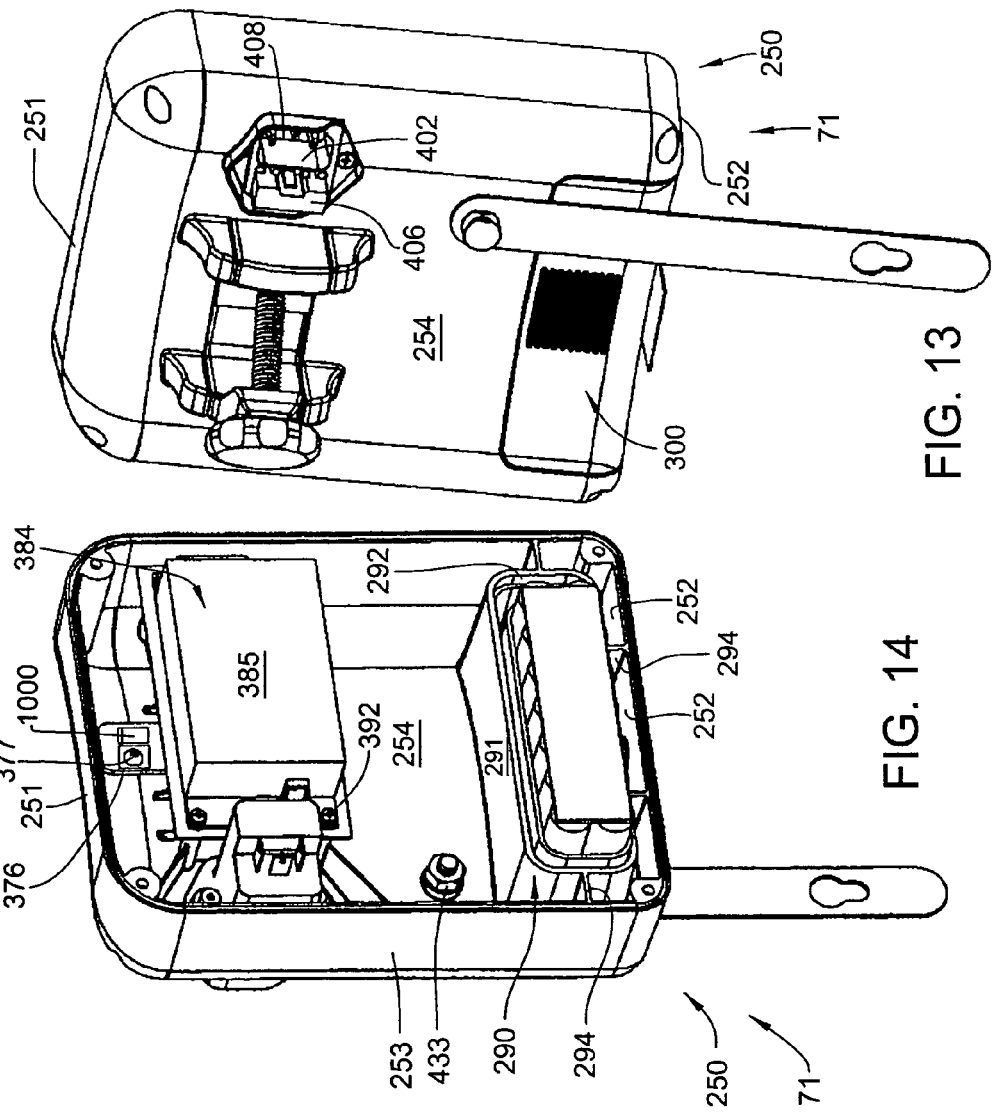

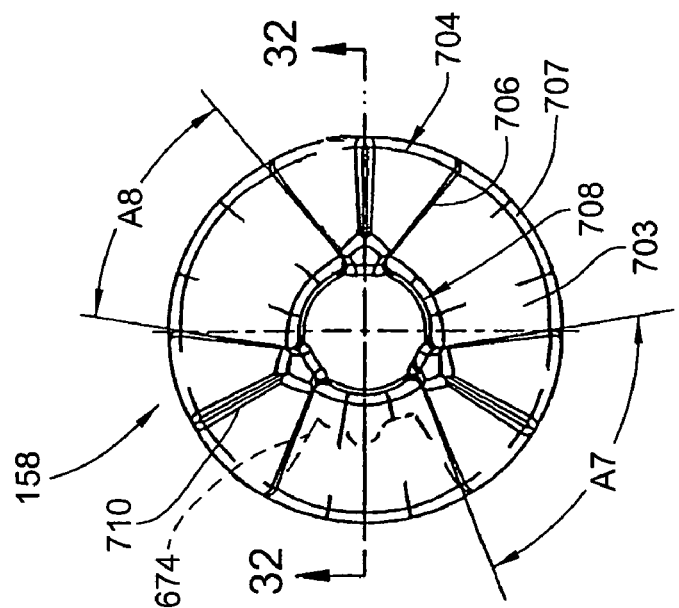
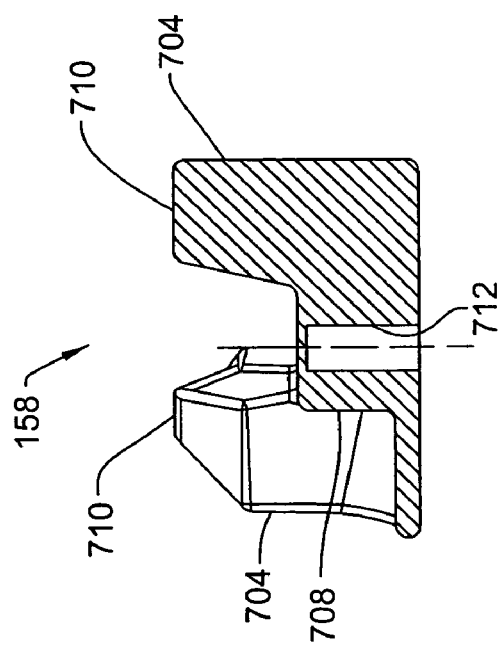
FIG. 32A
FIG. 32

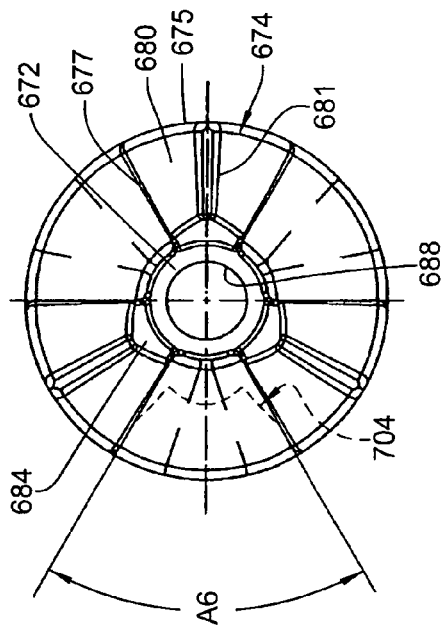
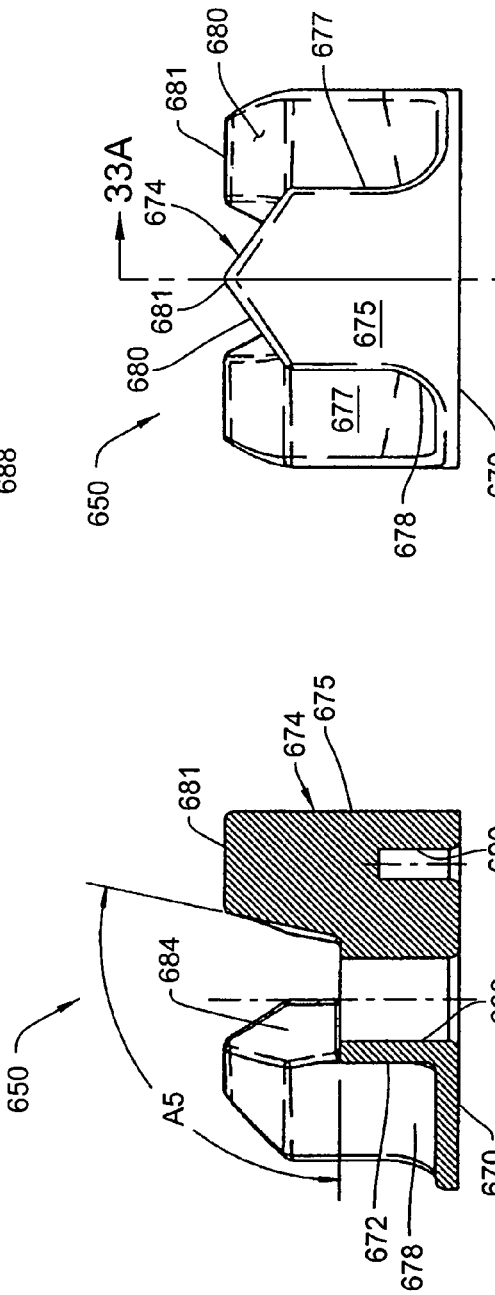
FIG. 33
FIG. 33B
FIG. 33A

SURGICAL IRRIGATION SYSTEM

CROSS-REFERENCE TO RELATED APPLICATIONS

This application claims the benefit of U.S. Provisional Application Ser. No. 60/750,102, filed Dec. 14, 2005, which is incorporated herein in its entirety.

FIELD OF THE INVENTION

This invention relates to a surgical irrigation system, and more particularly relates to an irrigation apparatus having a pump cassette separable from the power unit.

BACKGROUND OF THE INVENTION

Surgical irrigation apparatus, of the type having portions engageable with a surgical site and including a pumping member separably engageable with a power unit including a motor for driving the pumping member, is known in the prior art. A number of examples exist. However, those of which applicants are aware have variously provided room for improvement in terms, for example, of performance, convenience of use, reliability, cost, etc.

Accordingly, the objects and purposes of the invention include providing an improved apparatus of the aforementioned general type.

Further objects and purposes of the invention will be apparent to persons of ordinary skill in this art upon reading the accompanying description and inspecting the accompanying drawings.

SUMMARY OF THE INVENTION

This invention relates to a surgical irrigation system having an improved reusable motorized console and separable/attachable irrigation pump cassette, at least in one embodiment with improved mechanical and electrical inter-connecting structure therebetween and in at least one embodiment with pump priming structure and methods.

BRIEF DESCRIPTION OF THE DRAWINGS

FIG. 6 is an exploded pictorial view of the FIG. 4 power unit taken substantially from the left side and front and with the front end rear console assemblies thereof separated.

FIG. 7 is a pictorial view of the front console assembly of FIG. 6, taken substantially from the front thereof.

FIG. 8 is a further pictorial view of the FIG. 6 front console assembly taken substantially from the rear thereof.

FIG. 13 is a pictorial view of the FIG. 6 rear console assembly taken substantially from the rear and left side thereof.

FIG. 14 is a further pictorial view of the FIG. 13 rear console assembly but taken substantially from the rear and right side thereof.

FIG. 32 is a central cross sectional view of the motor coupler of FIG. 9, and substantially as taken on the line 32-32 of FIG. 32A.

FIG. 32A is a front end view of the motor coupler of FIG. 32.

FIG. 33 is a side view of the cassette coupler of FIG. 29.

FIG. 33A is a central cross sectional view substantially taken on the line 33A-33A of FIG. 33.

FIG. 33B is a rear end view of the cassette coupler of FIG. 29.

In the following description, the words up, down, right, left, front and rear, and derivatives thereof shall apply to directions in a given drawing figure and shall not be limiting.

DETAILED DESCRIPTION

A surgical suction irrigation system 10 (FIG. 1) comprises a surgical irrigation apparatus 12 comprising a console (or power unit) 14 and a cassette unit 16 releasably fixable to and removable from the console 14. The console 14 is intended to be reusable, in that it does not come in to contact with liquids that in turn make contact the patient at the surgical site on the patient, and because there is an economic saving in being able to reuse the console in subsequent surgeries. On the other hand, the cassette unit 16 is intended to be non reusable and disposable after use in a single surgery because it does handle irrigation liquid which may come into contact with the patient at the surgical site thereon, thus avoiding the risk of cross contamination from patient to patient and wherein the cassette unit may be manufactured at relatively low cost to minimize the economic impact of discarding after a single surgical use. However, it will be understood that the present invention is not limited to reusability or non-reusability of parts of the surgical system 10.

Figure 1:
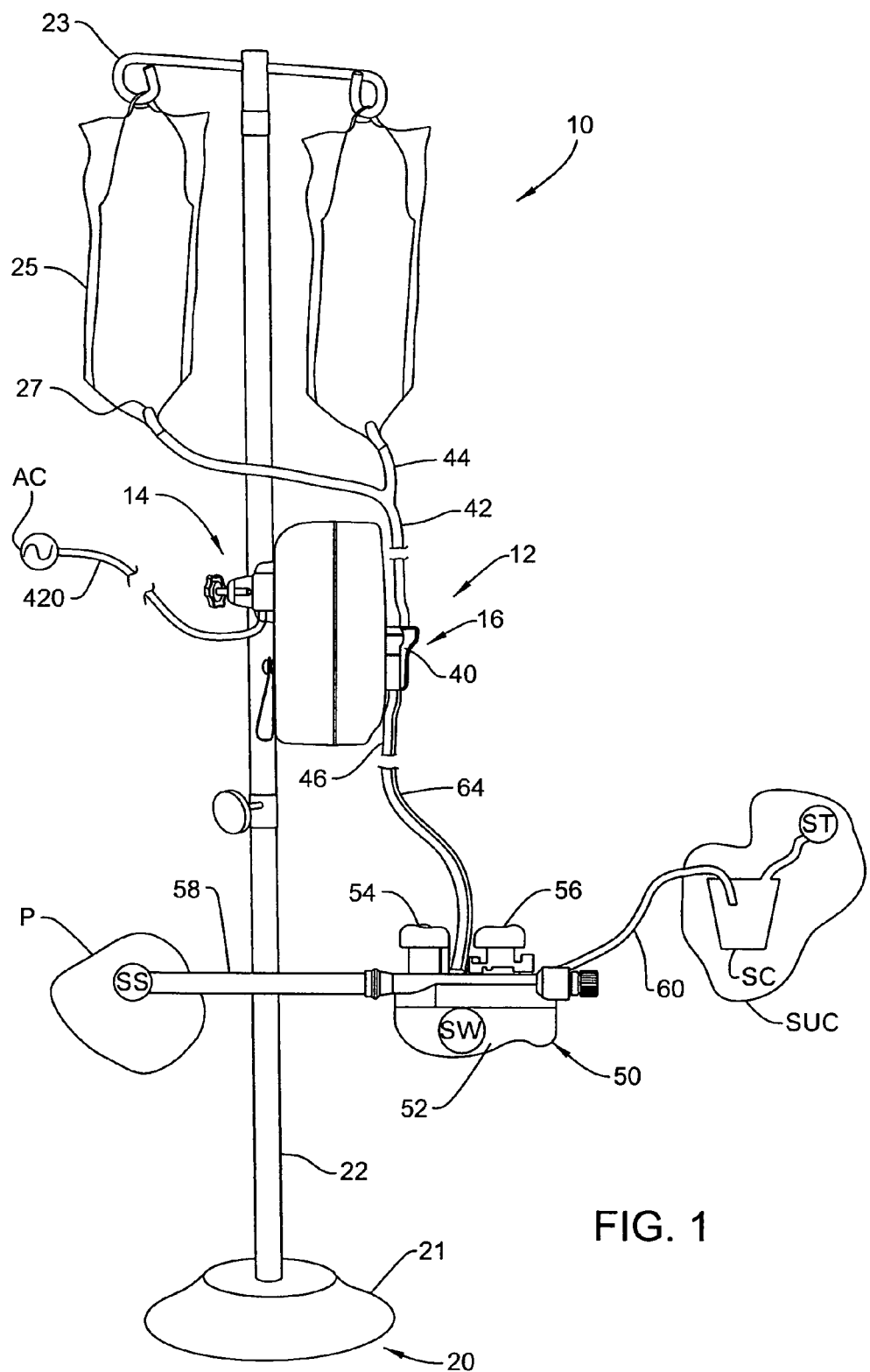
FIG. 1 is a pictorial, substantially schematic view of a surgical suction irrigation system embodying the invention.
Figure 2:
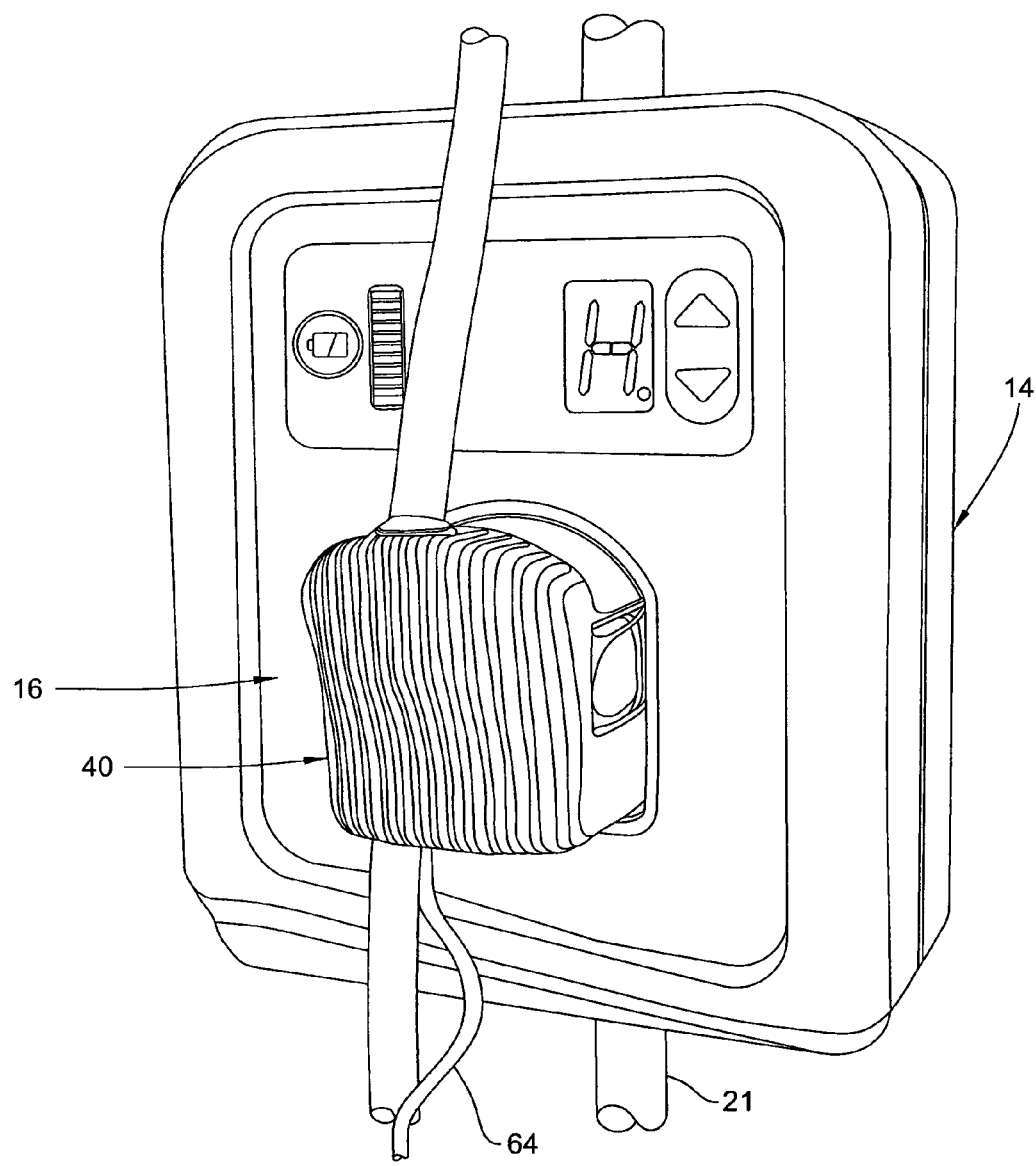
FIG. 2 is a pictorial view, taken substantially from the front and right side, of the surgical irrigation apparatus of FIG. 1.
Figure 2A:
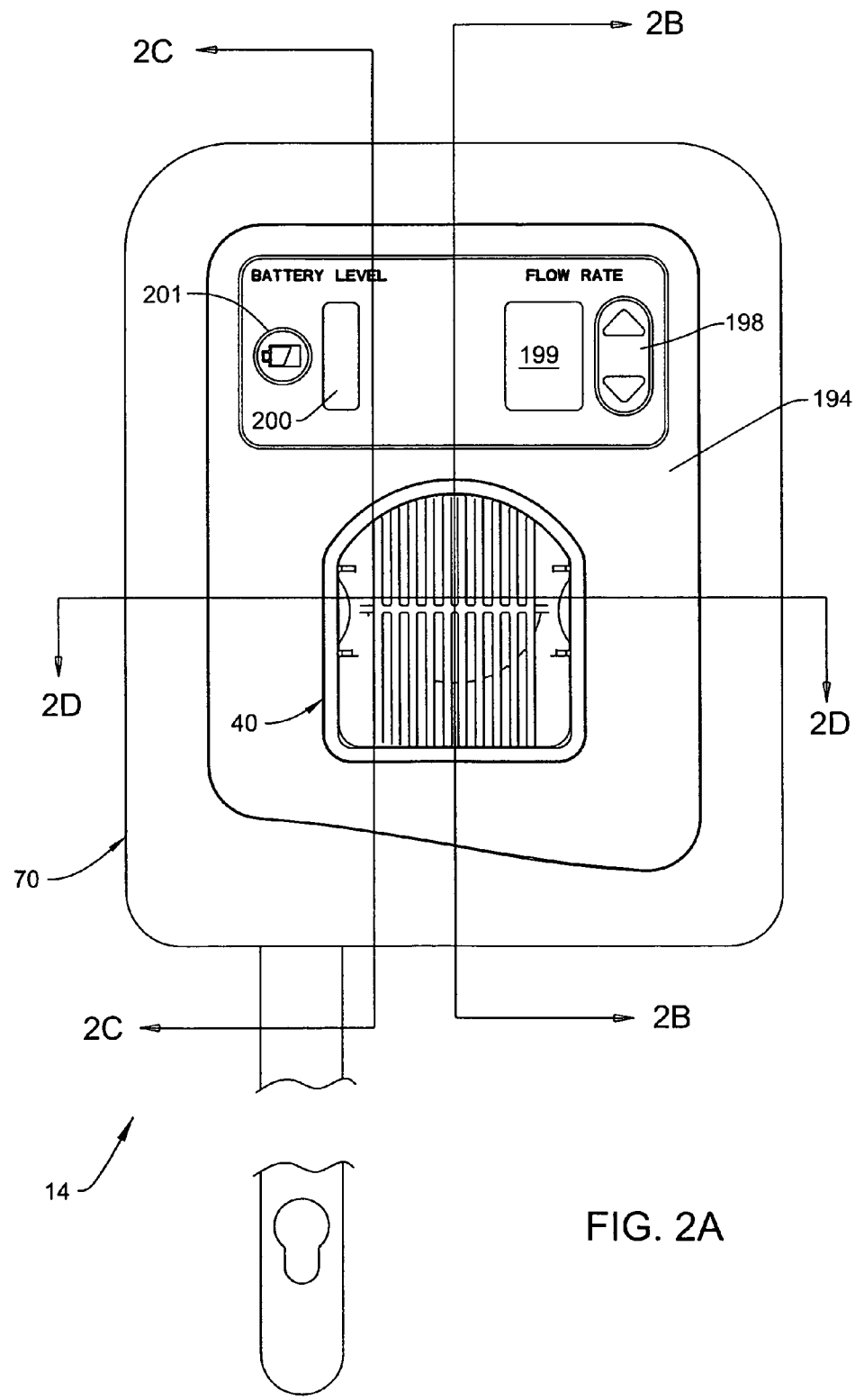
FIG. 2A is a front view of the FIG. 2 console 14 and cassette unit.

FIG. 1 schematically shows the surgical irrigation apparatus 12 in a typical position of use. As seen, the console 14 (FIGS. 1-3) is clamped at a desired height on a conventional upstanding (usually portable) support pole assembly 20, comprising a normally floor supported base 21, a pole 22 upstanding therefrom, laterally extending arms 23 fixed adjacent the upper end of the pole and adapted to pendantly support one or more (here two) irrigation liquid containers, typically bags, 25 having respective conventional fittings 27 communicating through the bottom thereof.

The cassette unit 16 includes a pump cassette 40 releasably fixed to the console 14, and irrigation liquid inlet tube 42 for receiving irrigation liquid from at least one of the irrigation liquid bags 25 (here through a "Y" tube 44) and flow control structure such as conventional manually operable tube pinch clamps, not shown, such that the surgical team can control gravity flow of irrigation liquid from the irrigation liquid bags to the irrigation liquid inlet tube 42 in a conventional matter.

The cassette unit 16 further includes an irrigation liquid outlet tube 46 to a surgical irrigation handpiece 50 of the type normally handled and controlled by a member of the surgical team (e.g. surgeon) for selectively applying irrigation liquid to a surgical site SS on a patient P. While the use of surgical irrigation handpieces of a variety of types is contemplated, preferred examples include those disclosed in U.S. Pat. Nos. 6,213,970 and 6,652,488 assigned to the assignee of the present invention.

The disclosure in those patents is incorporated by reference herein. Briefly summarizing however, the handpieces disclosed therein comprise, as schematically indicated in FIG. 1, a handpiece body 52 containing a normally closed, manually openable push button irrigation valve 54 and a normally closed, manually openable, push button suction valve 56 and having a forward extending, elongated tubular tip 58 insertable in a surgical site SS of a surgery patient P. A conventional suction tube 60 connects the handpiece 50 to a conventional suction source SUC. Thus, manual depression of the push button irrigation valve 54 directs a desired flow of irrigation liquid from the pump cassette 40 and the irrigation liquid outlet tube 46 through irrigation valve 54 and the tip 58 to the surgical site SS. On the other hand, manual depression of the push button suction valve 56 opens same to apply a desired level of draw liquid and other flowable material from the surgical site SS through the tip 58, handpiece suction valve 56, and suction tube 60 to the suction source SUC. The latter preferably conventionally includes a suitable suction container SC, maintained at subatmospheric pressure, as by connection to a conventional suction terminal ST in the surgical operating room wall for receiving and storing, for later disposal the flow of materials from the surgical site SS. Also, in the above listed patents incorporated by reference herein, the handpiece 50 includes a normally closed switch SW operatively connected by a multi-conductor (at least 2 wire) cable 64 to the surgical irrigation apparatus 12 in a manner hereafter more fully discussed.

It will be understood that the present invention is not limited to any particular type of handpiece or other connection to the surgical site SS, but rather that the handpiece 50 above discussed is disclosed for purposes of illustration only.

Turning now in more detail to the console 14 (FIGS. 4-6), same comprises a front console assembly 70 and a rear console assembly 71.

The front console assembly 70 (FIGS. 7-11) comprises a front chassis 80 of generally rectilinear, box-like, rear opening shape, comprising top and bottom walls 81 and 82, side walls 83, and a front wall 85. A generally centered, generally rectilinear, shallow recess 90 occupies most of the front of the front chassis, leaving a relatively thin border of front wall 85 bounding same. The front facing wall 91 of the recess 90 is pierced by a pair of generally rectangular, upstanding, upper holes 92 and 93 and, therebelow, a cassette receiving recess 96. The recess 96 is of generally rectilinear, upstanding form, though with a convexly rounded top wall 97. A generally tubular shell 100 opens through and extends forwardly from the back wall 98 of the cassette receiving recess 96.

Figure 10:
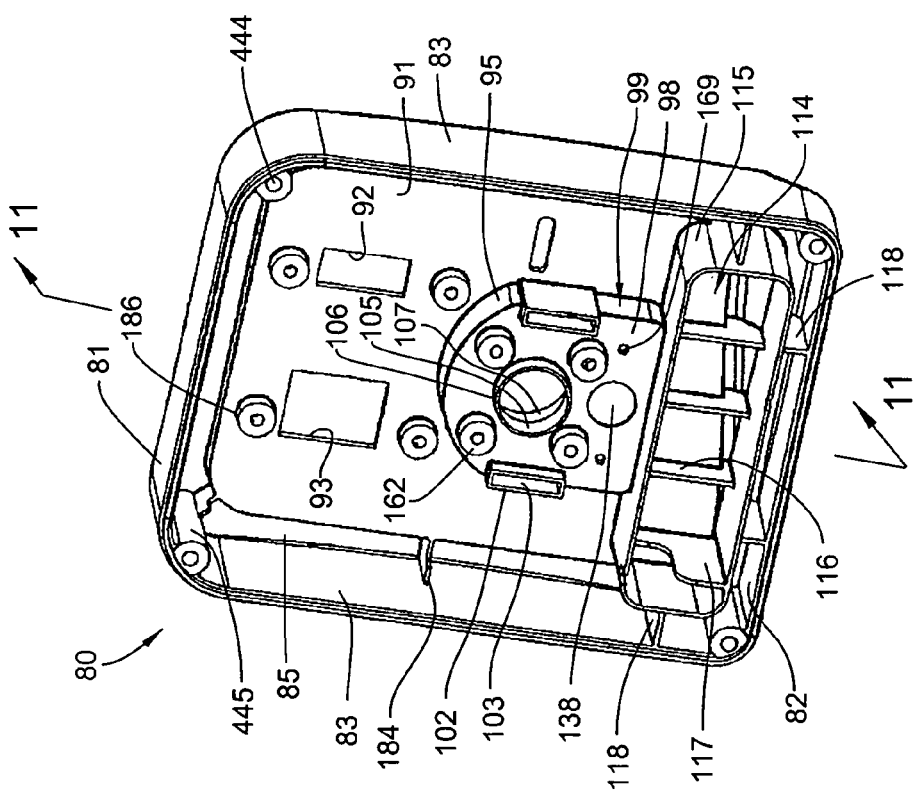
FIG. 10 is a pictorial view, taken substantially from the rear thereof, of the front chassis of the FIG. 9 front console assembly.
Figure 11:
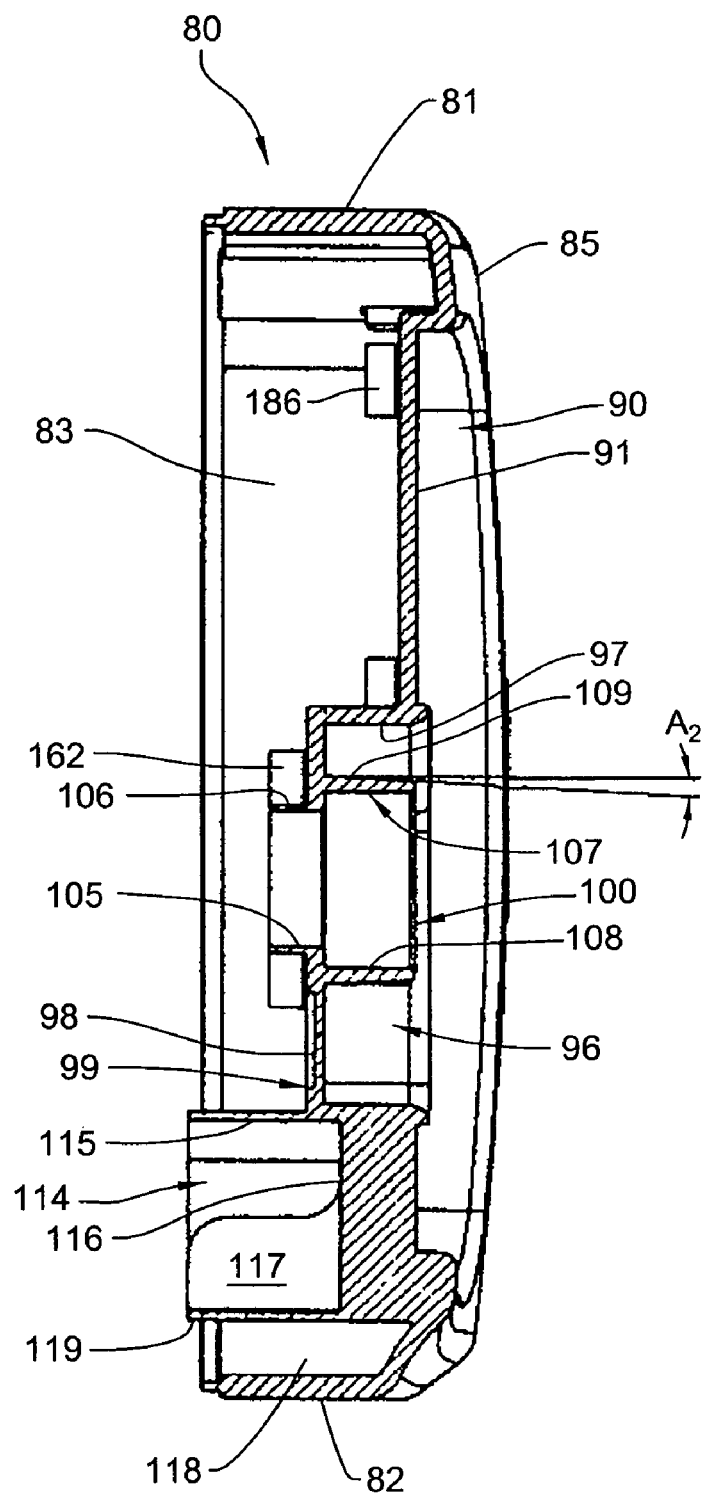
FIG. 11 is a central cross sectional view, substantially taken on the line 11-11, of FIG. 10.
Figure 12:
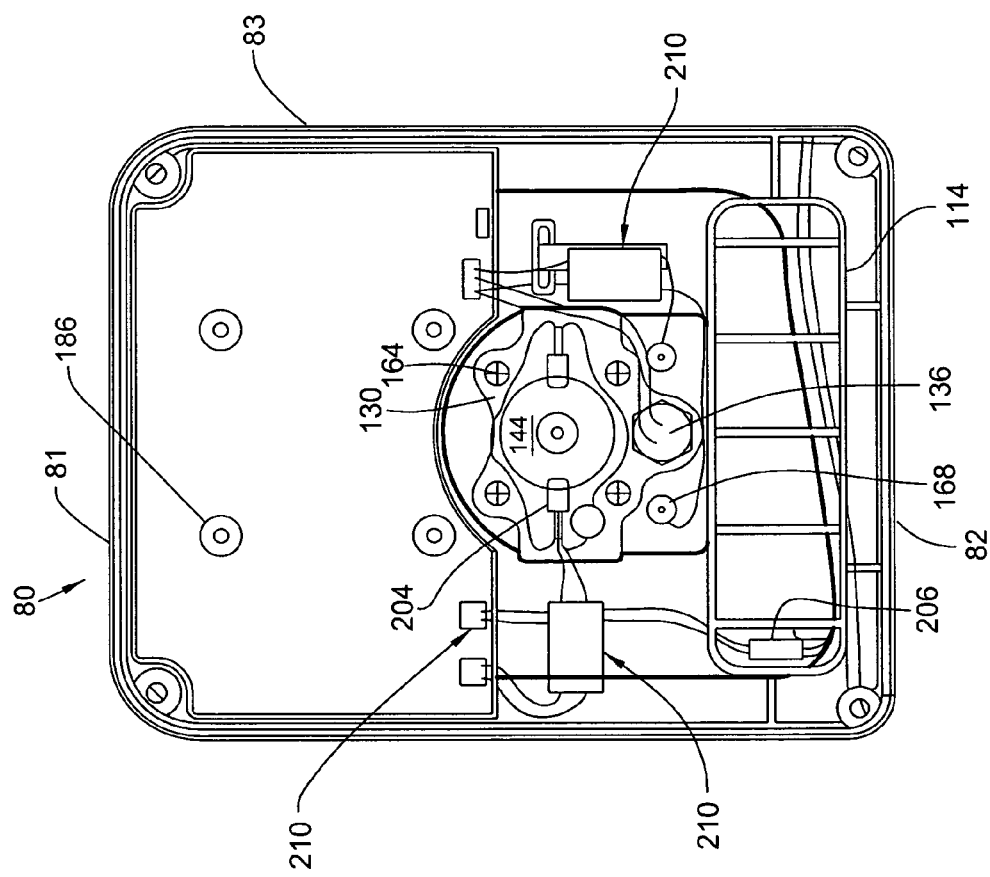
FIG. 12 is a rear view of the FIG. 8 front console assembly.

As seen from the rear in FIG. 10, the cassette receiving recess 96 forms a correspondingly shaped, rearwardly extending boss 99, beyond which the front chassis walls 81, 82, and 83 rearwardly extend. Upstanding, rectangular cross-section bezels 102 (FIGS. 10 and 11) protrude slightly rearward from the boss 99 and define forward/rearward opening through slots 103 for cassette mounting purposes as hereafter described. The bezels 102 are disposed at opposite sides of the boss 99 and flank the tubular shell 100 in laterally spaced relation on opposite sides thereof. The tubular shell 100 has a coaxial bezel 106 extending rearwardly from the boss rear wall 98 substantially to the extent of the cassette mounting bezels 102, and a central through hole 105. The central through hole 105 has an increased diameter, forward facing recess in the portion of the tubular shell 100 which extends forward from the back wall 98 (FIG. 11).

A laterally elongate, generally rectilinear, rearward opening battery receiving well 114 (FIGS. 10 and 11) is defined by a perimeter wall 115 extending rearward from the bottom portion of the front chassis front wall 85 and front facing recess wall 91 and laterally spaced, upstanding, battery backing ribs 116, as well as an upstanding divider wall 117 adjacent the leftward (FIG. 10) end of the battery receiving well 114. Webs 118 extend laterally and downwardly from the battery receiving well peripheral wall 115 to rigidly locate the latter within the front chassis 80.

To facilitate precise location of the cassette unit 16 on the console 14, the peripheral wall of the forward facing recess 107 has its exterior annular surface 109 convergently angled forwardly at an angle A2, preferably in the range of 2 to 4 degrees, for example 3 degrees.

The front console assembly 70 further includes a motor mount plate 130 (FIG. 9), generally of laterally extended rectilinear profile, having laterally spaced upper lobes 132 and a depending, central, lower lobe 133. A hole 134 in the lower lobe 133 receives a generally cylindrical proximity sensor 136, which is externally threaded and fixed to the plate 130 by sandwiching front and rear nuts 137, such that a portion of the sensor protrudes forwardly from the mounting plate 130 to engage a shallow rear facing circular recess 138 (FIG. 10) rearwardly opening in the back wall 98 (FIG. 10) of the front chassis 80.

An electric rotate motor 144 (FIG. 9) has a reduced diameter front boss 145 from which coaxially extends the rotatable shaft 146 of the motor. A resilient motor vibration damping gasket 148 sleeves snuggly over the front boss 145 and rests against the rear face of the motor mounting plate 130. The boss 145 and shaft 146 are forwardly received through a generally central hole 150 in the plate 130, with the shaft 146 extending forwardly well beyond the plate 130. Screws 152 extend rearwardly through screw holes laterally flanking the hole 150 in the plate 130, through corresponding holes in the gasket 148, and threadedly engage the front end of the motor 144 to fixedly cantilever the motor 144 from the rear face of the plate 130.

A motor coupler 158, hereafter more fully described, is fixed to the front end of the motor shaft 146, so as to be rotatable thereby.

The immediately above described proximity sensor/motor subassembly 130-158 is, during assembly of the front console assembly 70, fixed to the front chassis 80 by movement forward (rightward in FIG. 9) toward the back of the front chassis 80, to rest the front face of the plate 130 against internally threaded lugs 162 (FIG. 10). The latter extend rearward preferably into coplanar relation with the rear edges of the bezels 102 and loosely circumferentially surround the central bezel 106. Screws 164 (FIG. 9) extend through suitable holes in the top and bottom portions of the motor mounting plate 130 and thread into the lugs 162 (FIG. 10) to mount the sensor/motor subassembly 130-158 fixedly against the lugs 162 and bezels 102, with the motor shaft 146 and motor coupler 158 extending forward through the central through hole 105 and forward facing recess 107 of the front chassis 80 generally in the manner indicated in FIGS. 4, 6-8 and 12.

Figure 9:
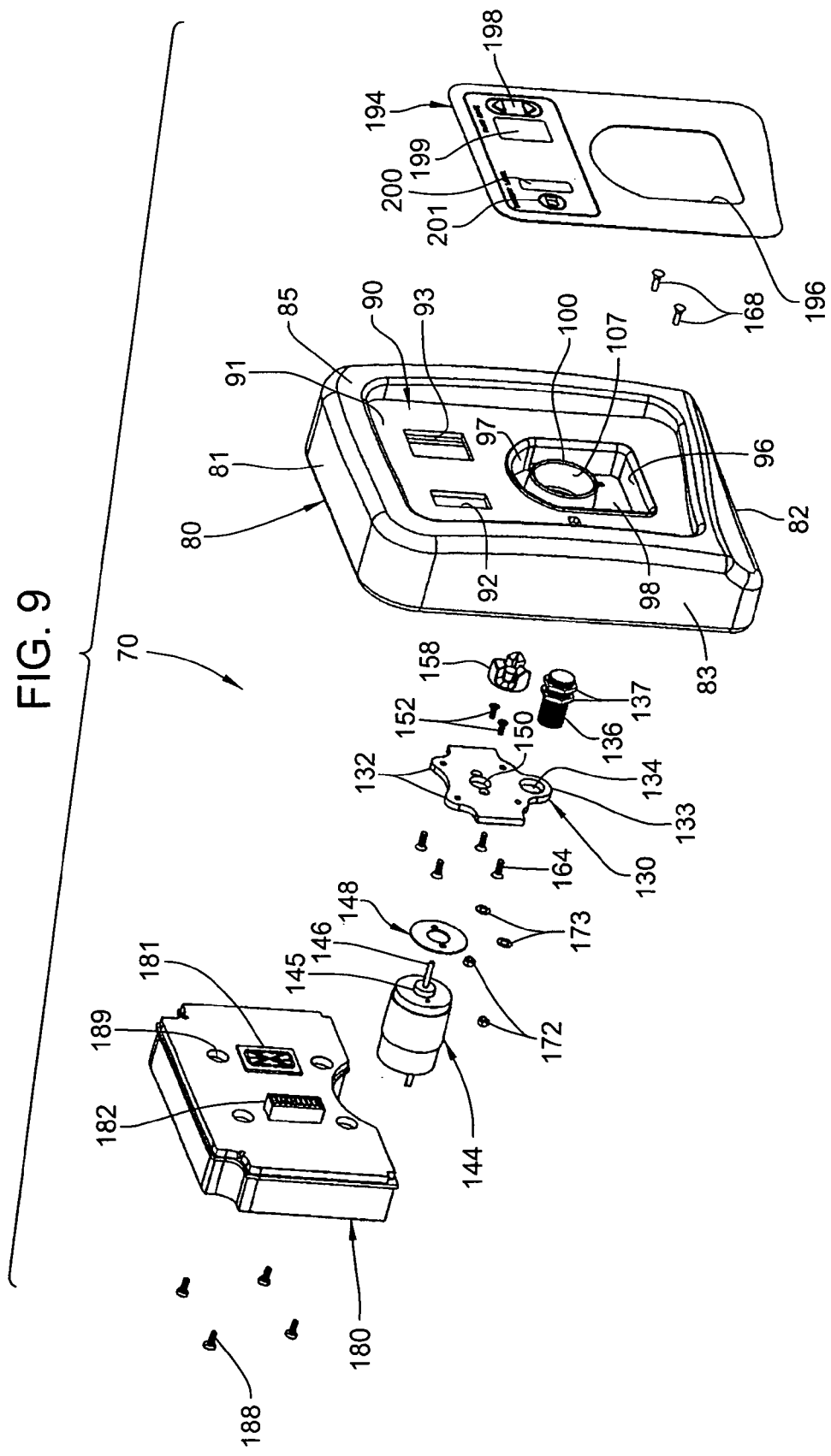
FIG. 9 is an exploded pictorial view of the FIG. 7 front console assembly.

A pair of console face plate contacts 168, here in the form of electrically conductive, panhead machine screws, extend, as generally indicated in FIGS. 7-9, rearwardly through holes 169 (FIG. 10) in the back wall 98 of the boss 99. Nuts 172 (FIG. 9), preferably with lock washers 173, fix the contacts 168 in place and connect same to the bared ends of corresponding electrical conductors 174 and 175 (FIG. 12) for purposes appearing hereafter.

A control board 180 (FIG. 9) carries control circuitry hereafter discussed on its rear face and on its front face carries a conventional digital flow rate display 181 and battery level display 182. To assemble, the control board 180 is inserted forward into the upper part of the open rear of the front chassis 80, into contact with webs 184 (FIG. 10) fixed to and extending rearward from the front wall 85 of the front chassis 80 and into supported contact with bosses 186 protruding rearward from the wall 91. The displays 181 and 182 extend into the holes 93 and 92, respectively, in the wall 91, so as to be visible from in front of the front chassis 80. Screws 188 (FIG. 9) extend through holes 189 in the control board 180 and are threaded into threaded holes in the aforementioned bosses 186 to fix the control board 180 in the open rear portion of the front chassis 80 adjacent the top wall 81 thereof, as generally seen in FIG. 8.

A cassette pump console membrane 194 (FIG. 9) is sized to fit in the main recess 90 (FIG. 9) of the front chassis 80 and has a through hole 196 sized and shaped and located to conform to the cassette receiving recess 96. The membrane 194 in its upper portion includes (1) a conventional membrane-type, finger pressure activated, upward shifting and downward shifting actuator 198, and immediately to the left thereof (2) a transparent window 199 through which the digital flow rate display 181 is visible, (3) a transparent window 200 through which the battery level display is visible, and (4) a battery check switch actuator 201 (preferably another membrane-type switch) finger pressure activated for manual checking of battery condition, e.g. when the apparatus is off and prior to use. The membrane 194 is fixed in any convenient manner, such as adhesive bonding, to the front facing wall 91, within the main recess 90.

The console face plate contacts 168 (FIG. 12), a set of electrical energizing contacts 204 on the motor 144, a battery connector 206, and the proximity sensor 136 are connected by suitable wiring generally indicated at 210 to the control board 180 (FIG. 9) in a manner hereafter discussed.

Turning now to the rear console assembly 71 (FIGS. 13-15), same comprises an open front, generally rectilinear box-like rear chassis 250 having a top wall 251, a bottom wall 252, side walls 253 and a rear wall 254. In the embodiment shown, the rear wall 254 is concavely curved about a distant vertical axis not shown.

The corners and edges of the front chassis 80 and rear chassis 250 are preferably curved on a relatively large radius, as shown, for comfort and ease of handling.

The rear chassis rear wall 254 (FIGS. 16 and 17) in its upper portion, has a rear opening, laterally extending, generally rectilinear clamp recess 260 having an inboard base wall 261 and perimeter walls 262. Stiffening webs 263 (FIGS. 15 and 17) extend from the clamp recess perimeter wall 262 to the rear chassis rear wall 254 for stiffening purposes. Generally rectilinear struts 266 extent rearwardly from the rear wall 254 at the top and bottom edges of the clamp recess 260 and are laterally spaced apart so as to lie substantially flush with the plane of the laterally imposed ones of the recess perimeter walls 262. The struts 266 have vertically opposed, substantially parallel faces 267 which are preferably flush with the opposed top and bottom ones of the recess perimeter walls 262. In the preferred embodiment shown, the struts have faces which are vertically remote from the clamp recess 260 and are preferably curved in approximately an S-profile, so as to be convexly rounded at their outer (rearward) ends and concavely curved into substantially filleted engagement with the chassis rear wall 254, as generally indicated at 268. The recess 260 and struts 266 define a clamp mount generally indicated at 270.

An AC power cord mount 280 (FIG. 16) comprises a preferably rectangular, substantially square hole 281 through the rear wall 254, immediately to the right (in FIG. 16) of the clamp mount 270. The hole 281 opens rearward through a substantially diamond shaped recess 282 in the chassis rear wall 254, which defines upper and lower, substantially triangular shape, rearward facing flats 284. A bonnet brim 286 extends rearward from the chassis rear wall 254 flush with the laterally opposed side and top walls of the recess 282, in a manner to, for example, deflect falling water droplets from entry into the hole 281 and recess 282.

Figure 16:
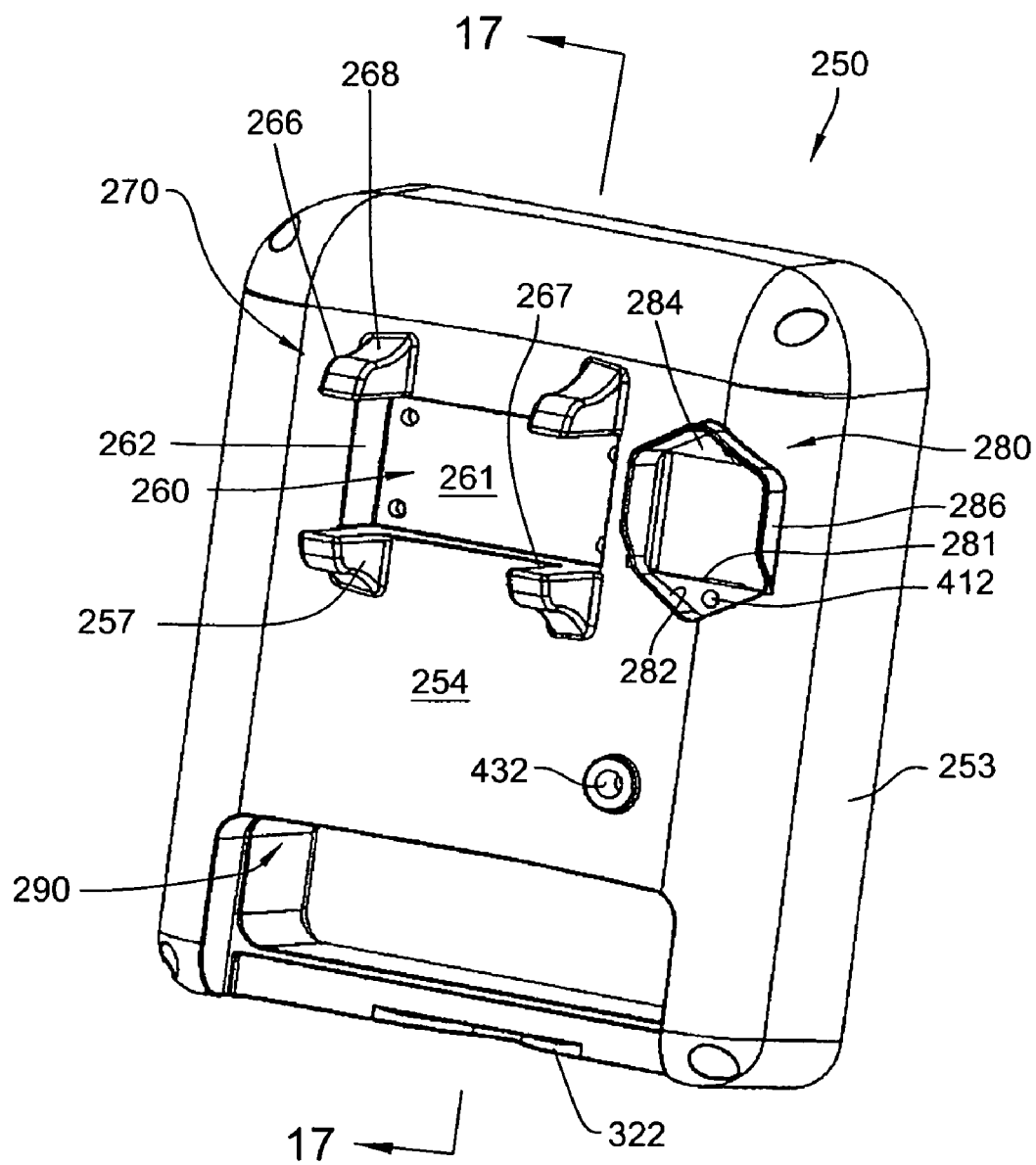
FIG. 16 is a pictorial view of the rear chassis of the FIG. 15 rear console assembly, taken substantially from the rear and left side thereof.
Figure 17:
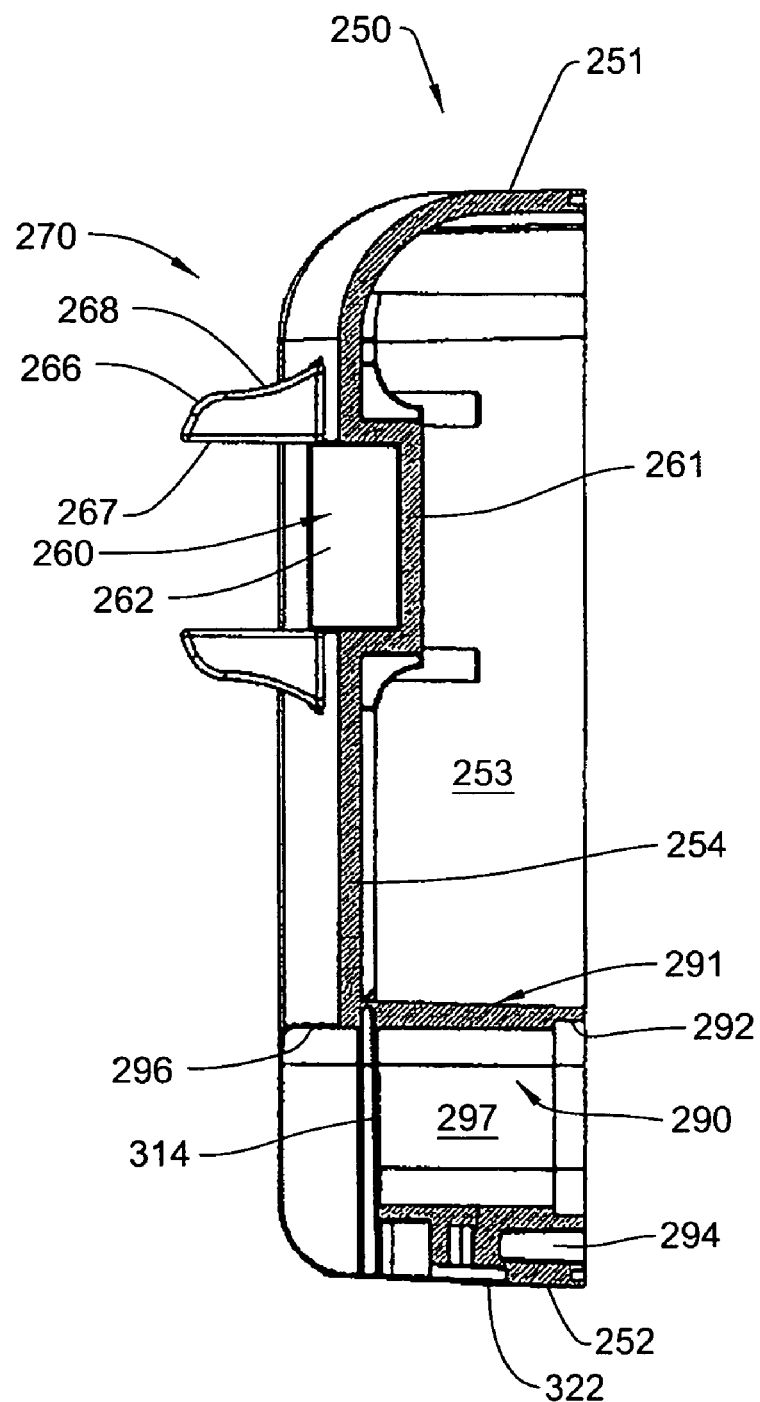
FIG. 17 is a central cross sectional view taken substantially on the line 17-17 of FIG. 16.

A laterally elongate, generally rectilinear, battery receiving passage 290 (FIG. 16) opens through the lower portion of the back wall 254. The passage 290 is located, shaped and sized to be a substantially flush rearward extension of the battery receiving well 114 of FIGS. 10 and 11. Indeed, the well 114 and passage 290 are preferably somewhat mutually telescoped upon assembling together of the front and rear console assemblies 70 and 71. More particularly, the peripheral wall 291 (FIG. 17) of the passage 290 has an axially relatively short, inner, front facing recess 292 that snugly telescopingly receives the rear edge portion 119 (FIG. 11) of the well peripheral wall 115 (FIG. 11). As seen in FIG. 11, the portion 119 projects slightly rearwardly beyond the top, bottom, and side walls 81-83 of the front chassis 80 to snugly fit in the recess 292 (FIG. 17). The result is that, in the assembled console 14, the interior surface of the passage peripheral wall 291 is a smoothly flush rearward extension of the interior surface of the peripheral wall 115 of the battery receiving well 114 (FIG. 11). In the preferred embodiment shown, webs 294 extend from the passage peripheral wall 291 laterally and downwardly to the side and bottom walls 253 and 252 of the rear chassis 250 to rigidify the location of the peripheral wall 291 within the confines of the rear chassis 250.

Figure 18:
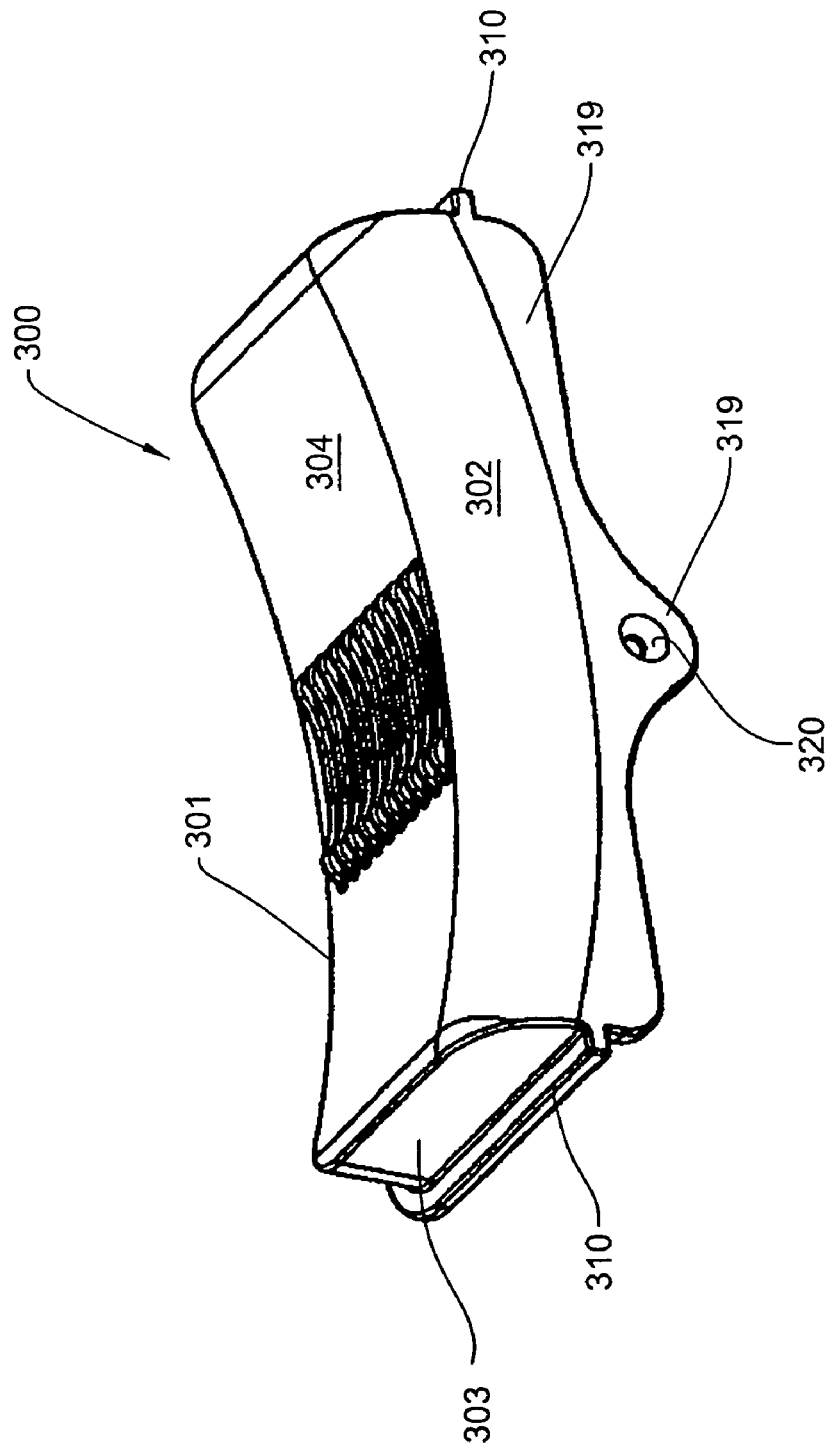
FIG. 18 is a pictorial view of the battery cover of FIG. 15 taken substantially from the bottom and rear thereof.

A shallow, box-like, generally rectilinear, forward opening battery cover 300 (FIGS. 15 and 18) is laterally elongate and has a back wall 304 from which forwardly protrude top and bottom walls 301 and 302 and upstanding side walls 303. The battery cover 300 is sized and shaped to install in the rear portion of the battery receiving passage 290, such that the battery cover bottom and back walls 302 and 304 are flush with the rear chassis bottom and back walls 252 and 254, as seen in FIG. 13. A rectangular cross section lip 319 extends along and protrudes perpendicularly from the forward edge of the battery cover top and side walls 301 and 303 and, upon upward movement of the battery cover 300 into closing relation with the rear portion of the passage 290, is snugly but slideably received in a corresponding guide groove 314 (FIG. 17) opening downwardly and laterally inwardly from the upper end wall portion 296 and side wall portions 297 of the battery receiving passage peripheral wall 291, so as to releasably fix the battery cover 300 against upward, sideward and forward/rearward movement out of its battery receiving passage closing position of FIG. 13. The bottom wall 302 of the cover 300 has a forward extending portion, or ledge, 318 (FIG. 18) including a central tip 319 having a preferably countersunk through hole 320. With the battery cover 300 installed on the rear chassis 250 as in FIG. 13, the tip 319 is received in a correspondingly profiled rearward and downward opening recess 322 (FIGS. 16 and 17) in the bottom wall 252 of the rear chassis 250 and is releasably retained by any convenient means such as an upwardly inserted screw 323. If desired, and as seen in FIG. 15, a semirigid plastic label 324, e.g. to warn the users of the need to connect the batteries before use, may be fixed by the screw 323 to the tip 319.

Figure 15:
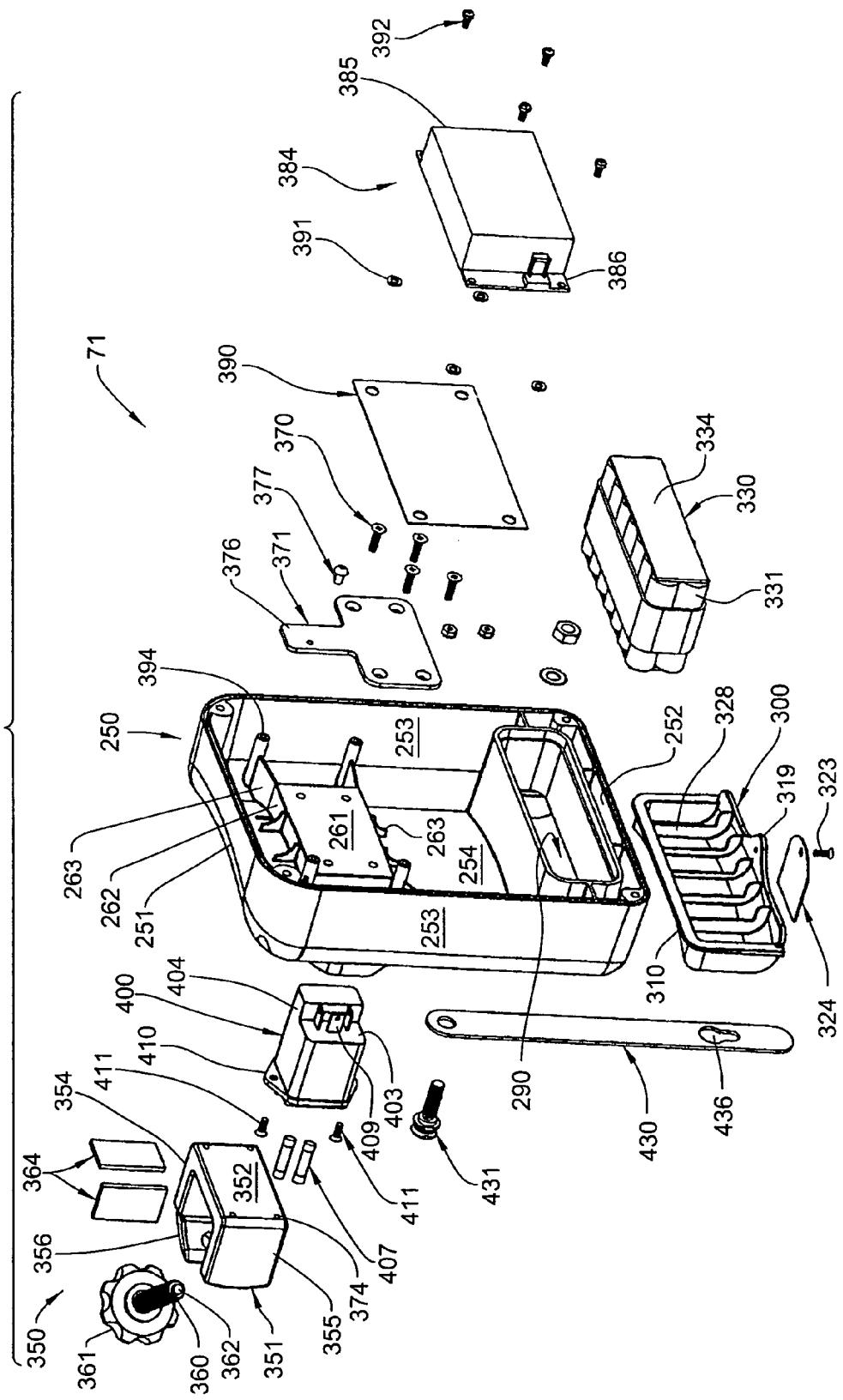
FIG. 15 is an exploded pictorial view of the FIG. 14 rear console assembly.
Figure 19A:
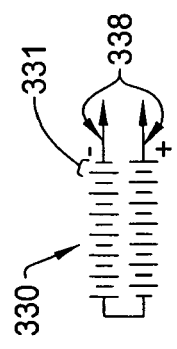
FIG. 19A is a schematic view of the FIG. 19 battery pack.
Figure 19:
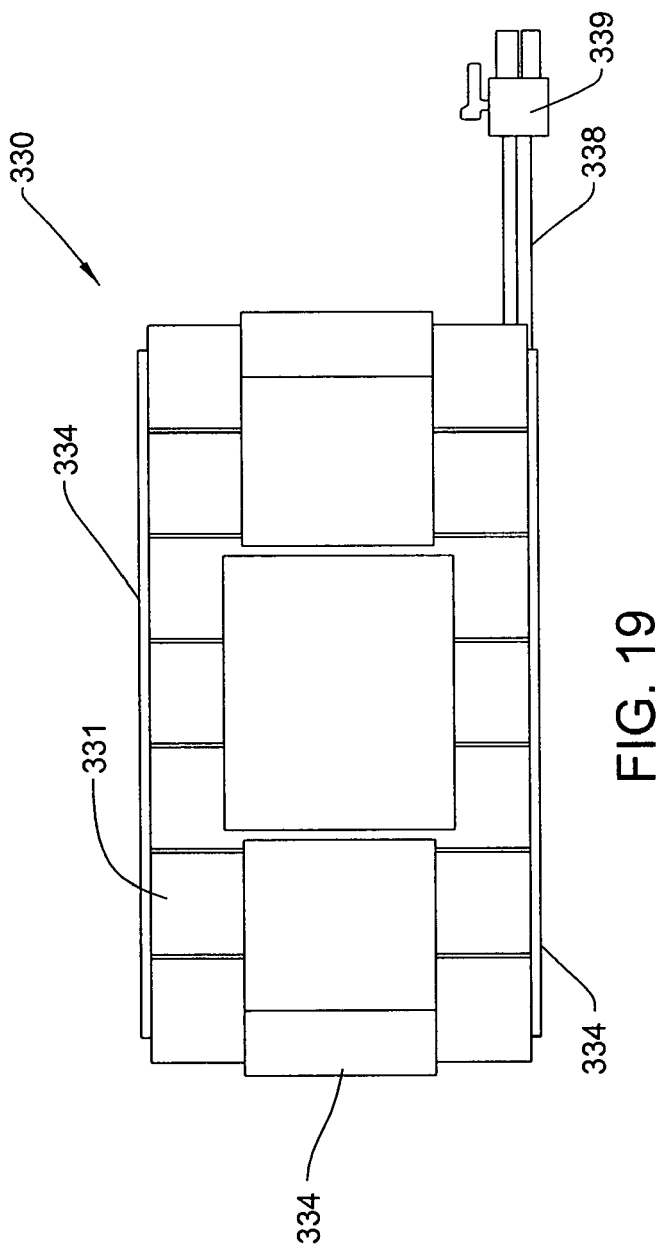
FIG. 19 is a bottom view of the battery pack of FIG. 15.

Generally L-profile webs 328 (FIG. 15) are laterally spaced and extend forward and upward from the bottom and back walls 302 and 304 of the battery cover 300 to block rearward and downward shifting of a battery pack 330 (FIGS. 15 and 19).

In the embodiments shown, the battery pack 330 (FIGS. 15 and 19) comprises a number of cells sufficient to provide the desired operating voltage, here for example 14 cells nominally rated at 1.2 volts apiece for a total nominal rating of 16.8 volts. While the battery pack 330 may be comprised of non-rechargeable (e.g. alkaline) cells, rechargeable cells are preferred, particularly conventional nickel metal hydride (NiMH) cells in view of their low toxicity, relatively high ampere hour capacity, and relatively flat voltage output under load and over a relatively high percentage of their total discharge capacity. Conventional AA cells are compact and widely available at low cost and so are preferred. In the embodiments shown, the individual cells 331 are packaged in a substantially brick-like form comprising two parallel, side-by-side rows of 7 cells apiece, fixedly secured together by any convenient means, for example heat shrink film (not shown).

Figure 5:
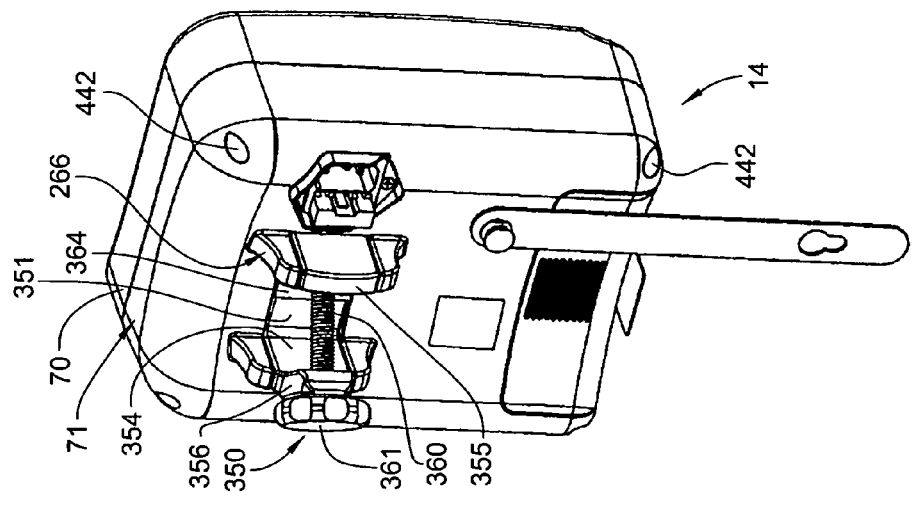
FIG. 5 is a pictorial view taken substantially from the rear and left side, of the FIG. 4 power unit.
Figure 4:
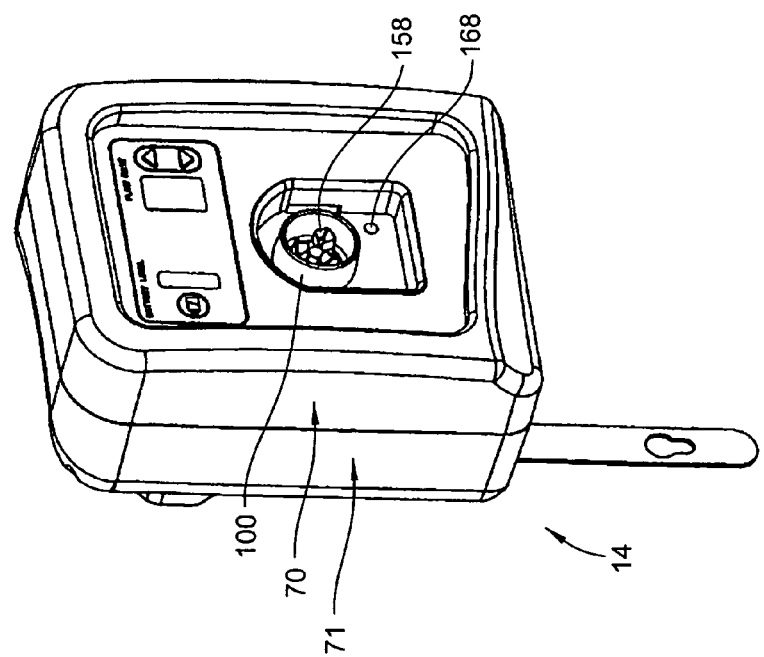
FIG. 4 is a pictorial view taken from the front and left side, of the console, or power, unit of the FIG. 2 apparatus, namely with the FIG. 2 pump cassette removed.

Electrical connections between the cells 331 are covered by the mentioned heat shrink film, as well as by padding preferably in the form of conventional adhesive backed foam sheets (sometime referred to as foam tape) 334 which snuggly and resiliently support the battery pack 330 when installed in the battery receiving passage 290 (FIG. 6) and battery receiving well 114 (FIG. 14) of the front chassis 80, upon assembly of the front and rear console assemblies 70 and 71 as appearing in FIGS. 4 and 5.

The battery pack 330 has insulated output wires 338 (FIGS. 9 and 19) variously of positive and negative polarity and which are connected to circuitry (hereinafter discussed) by any convenient means, here schematically indicated by a suitably mechanically lockable and releasable connector 339.

The base wall 261, above mentioned with respect to the clamp recess 260, mounts several interior and exterior components as immediately hereafter discussed with reference to FIGS. 14 and 15.

Figure 3:
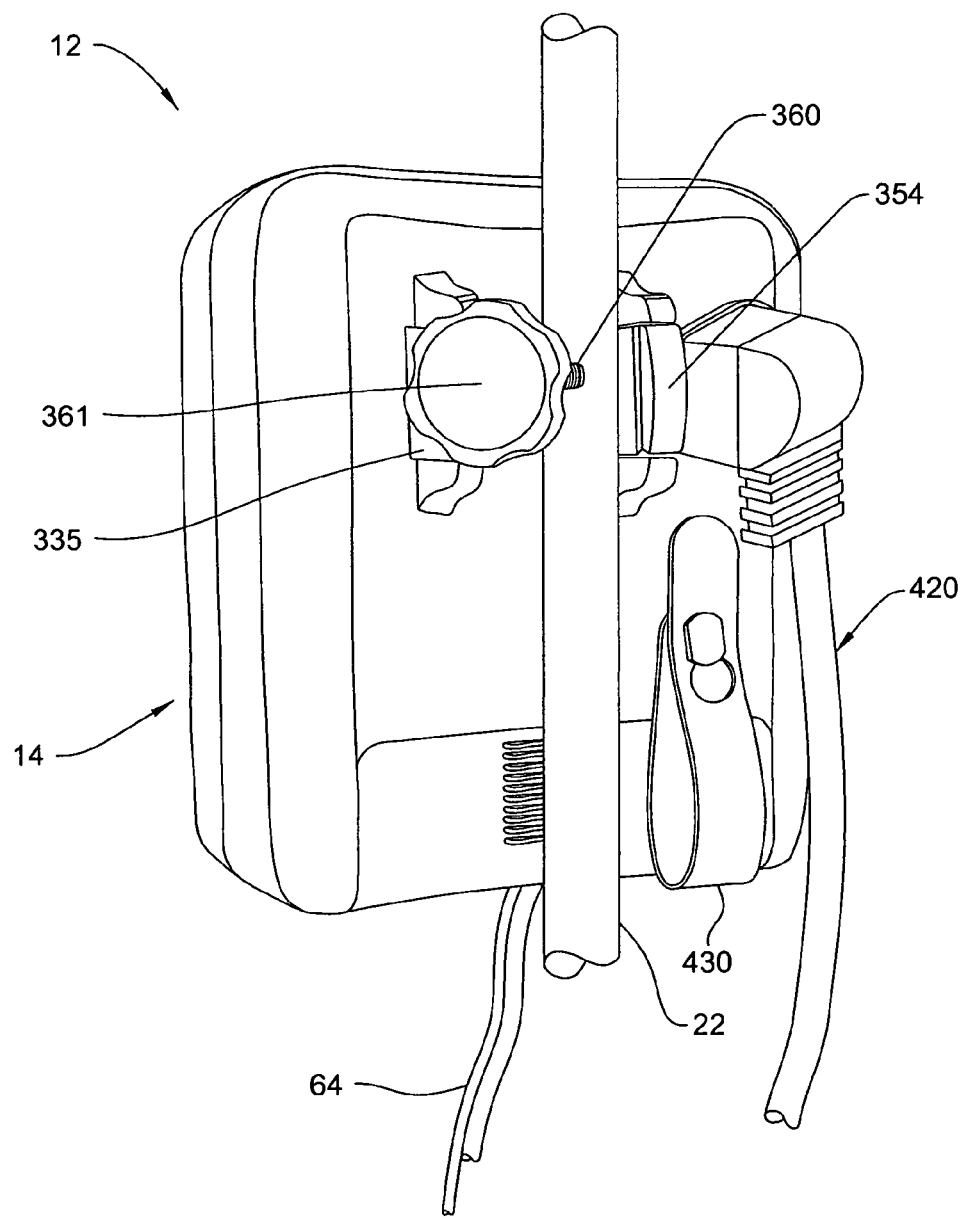
FIG. 3 is a pictorial view of the FIG. 2 apparatus taken substantially from the rear thereof and showing mounting thereof on a conventional, upstanding, irrigation liquid bag support pole.

A clamp assembly 350 (FIG. 15) comprises a generally C-shaped clamp base 351 having a laterally extending bight wall 352, from the ends of which rearwardly extend respective arms 354 and 355. A palm plate 356 angles rearwardly and laterally inwardly from the rear end of the arm 355. A clamp screw 360 extends threadedly through a threaded opening in a palm plate 356 and angles forwardly and toward to the joinder of the clamp base and arm 354. The outboard end of the clamp screw 360 defines a hand actuable knob 361. The clamp screw 360 at inboard end preferably fixedly carries a non-marring (e.g. rigid or resilient plastic) tip 362. The clamp assembly 350, as seen in FIG. 3, adjustably and releasably supports the surgical irrigation apparatus 12 on a support, such as the above mentioned support pole 22, by pocketing the latter in the pocket defined by the joinder of the clamp assembly bight wall 352 and arm 354 and holding same there by threading the inboard end of the screw 360 end into contact with such pole 22.

Friction pads 364 (FIG. 15) of any convenient surface textured, high friction, and preferably generally resilient, rubber-like material, here rectangular in shape, are fixed, conveniently by adhesive bonding, to the rear and laterally inboard faces of the bight wall 351 and arm 355 of the clamp assembly 350, adjacent to join of the bight wall 351 and arm 355, to frictionally engage the pole 22 (FIG. 3), and thereby assist the tightened screw 360 in fixedly clamping the console 14 to the pole 22. The bight wall 351 of the clamp assembly is snugly received in the clamp recess 260 (FIG. 16) against the base wall 261 thereof, with the arms 354 and 355 snugly vertically sandwiched between corresponding laterally spaced pairs of the struts 266, in the manner seen in FIG. 5.

Flat head mounting screws 370 (FIG. 15) extend rearward through countersunk holes in the substantially rectangular bottom portion of a generally inverted, T-profile clamp mounting plate 371 and thence through holes in the base wall 261 of the clamp recess 260 and thread in to forward facing holes 374 in the clamp base 351 (located in the present example at the four corners of the base 351) to fix the clamp assembly 350 in the clamp recess 260 in the back of the rear chassis 250, as seen for example in FIG. 5.

A power supply unit 384 (FIG. 15) comprises a substantially rectangular, laterally extended circuit board 386. The board 386 carries on its forward face suitable power supply circuitry, indicated schematically in FIG. 15 by the rectilinear block 385, and which faces forward from the circuit board 386. An electrical insulator sheet 390 of suitable insulative material, such as TEFLON®, faces forward toward the rear face of the circuit board 386. The spacers 391 allow for proper spacing between the power supply and the electrical insulator sheet. Screws 392 extend rearwardly through holes in the corners of the circuit board 386, the washer-like spacers 391, and thread into the front ends of bosses 394 extending forward from the rear wall 254 of the rear chassis 250. The holes in the insulative sheet 390 slide over bosses 394 on the rear chassis and is held in position between the power supply and the rear chassis. The bosses 394 engage ones of the above mentioned webs 263. The thus installed power supply unit 384 is seen in FIG. 14.

The relatively massive external C-shaped clamp base 351, the screws 370 and 377, and the plate 371 are preferably of heat conductive metal. In the embodiment shown, the clamp mounting plate 371 may include a laterally narrow, upstanding tab 376 (FIGS. 14 and 15) carrying a screw 377, which in one unit constructed according to the invention enabled use of the exterior clamp base 351 as a heat sink for a heat generating component of the power supply 384, here exemplified by a power resistor 1000 (FIGS. 14 and 34A across the power supply output.

A conventional power module 400 (FIG. 15), intended for connection to a remote conventional external power source (e.g. wall socket), such as a 110 volt AC source in the United States, may be of any commercially available type. In the embodiment shown, the power entry module 400 is a model 5220.0123.3 available from Schurter, Inc. located at Santa Rosa, Calif. In the example shown, same comprises an insulated body 404 having a rear opening recess 402 (FIG. 13) and a frontward and laterally opening notch 403 (FIG. 15). The body includes a portion 406 for receiving conventional fuses 407 (FIG. 15) interposed between rearward extending electric power inlet conductors 408 (FIG. 13) in the recess 402 and output conductors 409 in the notch 403. The inlet conductors 408 are conventionally shaped, spaced and oriented for connection to a conventional "house" power line e.g., in the United States a 110 volt AC wall plug, through a conventional power cord unit 420 (FIGS. 1 and 3). The power entry module 400 here includes upward and downward extending ears 410 (FIG. 15). Screws 411 extend forwardly through holes in the ears 410 and into threaded engagement with rear facing holes 412 (FIG. 16) in the triangular flats 284 in the AC power cord mount 280.

A flexible cord holder strap 430 (FIG. 15) is pivotally fixed at its upper end by a screw 431 on the rear face of the rear wall 254 of the rear chassis 250. The screw 431 extends through a hole in the upper end portion of the strap 430, and thence through a hole 432 (FIG. 16) in the chassis rear wall 254 for threaded retention by a nut 433 (FIG. 14), which is preferably locked by lock washer or is of conventional self-locking type. Screw 431 has an annularly grooved axially elongated head 434 for receiving in the widened end of a keyhole 436 (FIG. 15) adjacent the lower end of the strap 430, such that the strap can be folded upon itself, as a loop, as seen in FIG. 3. When it is desired to shorten the power cord, loops of the midportion of the power cord unit 420 may be fixed to the rear face of the console 14 by means of the strap 430.

To assemble together the front and rear console assemblies 70 and 71 (FIGS. 4 and 5) to form the console 14, screws 440 (FIG. 6), preferably provided with washers 441, are inserted forwardly into deeply recessed rearward facing holes 442 extending forward through bosses 443 preferably located at the four corners of the box-like rear chassis 250 (FIG. 6) and thread into rearward opening holes 444 (FIGS. 8 and 10) extending forward into bosses 445 preferably disposed at the four corners of the interior of the box-line front chassis 80.

Turning now to the cassette unit 16 (FIG. 21), the pump cassette 40 comprises a cassette body 450 and a cassette cover subassembly 451.

The cassette body 450 is generally box-like in shape, opening rearwardly (leftwardly in FIG. 21) and comprising a bottom wall 460, laterally spaced upstanding side walls 461 and a convexly cylindrically rounded top wall 462, as well as a front wall 464.

The cassette body 450 (FIGS. 21-26) includes a cup-like, rear opening pump chamber 470 having a generally circularly cylindrical peripheral wall 471 extending rearward from the cassette body front wall 464. The pump chamber 470 comprises a rear opening cavity 482 bounded by a generally cylindrical front peripheral surface 474, a rear facing annular step 472, and a generally cylindrical rear inner peripheral surface 477 of increased diameter. A concavely curved annular fillet 479 connects the front peripheral surface 474 to a front end face 475, which faces rearward toward the open end of the pump chamber cavity 482. The step 472 extends radially inward from the front inner peripheral surface to the rear inner peripheral surface. The cassette body front wall 464 forms and extends forward from the pump cavity front end face 475.

Figure 21:
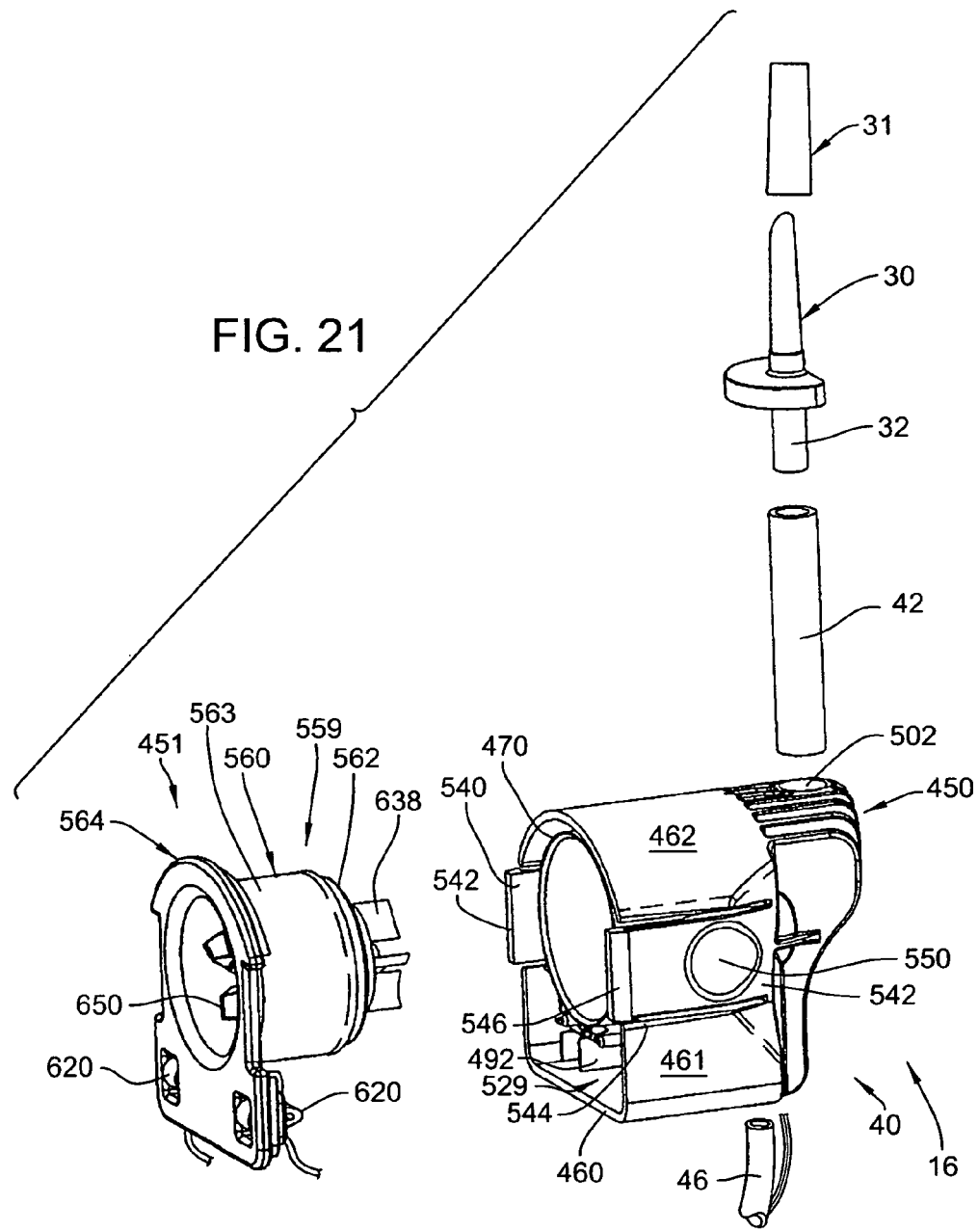
FIG. 21 is an exploded pictorial view of the cassette unit of FIG. 1.
Figure 22:
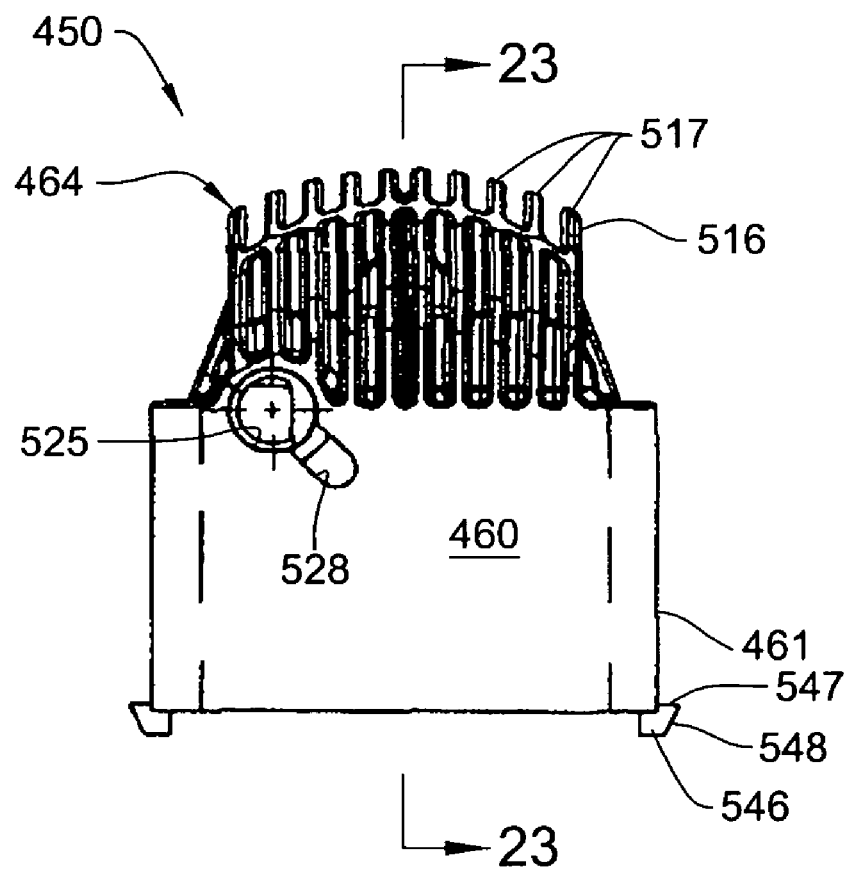
FIG. 22 is a bottom view of the cassette body of FIG. 21.
Figure 23:
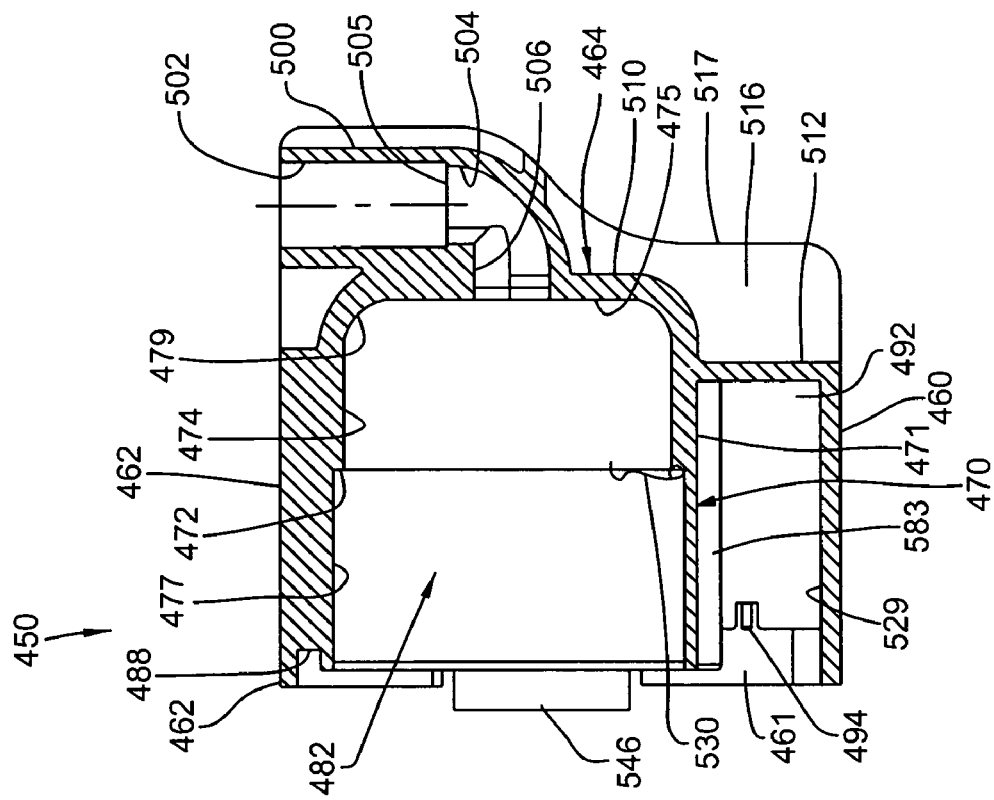
FIG. 23 is a central cross sectional view substantially taken on the line 23-23 of FIG. 22.
Figure 23A:
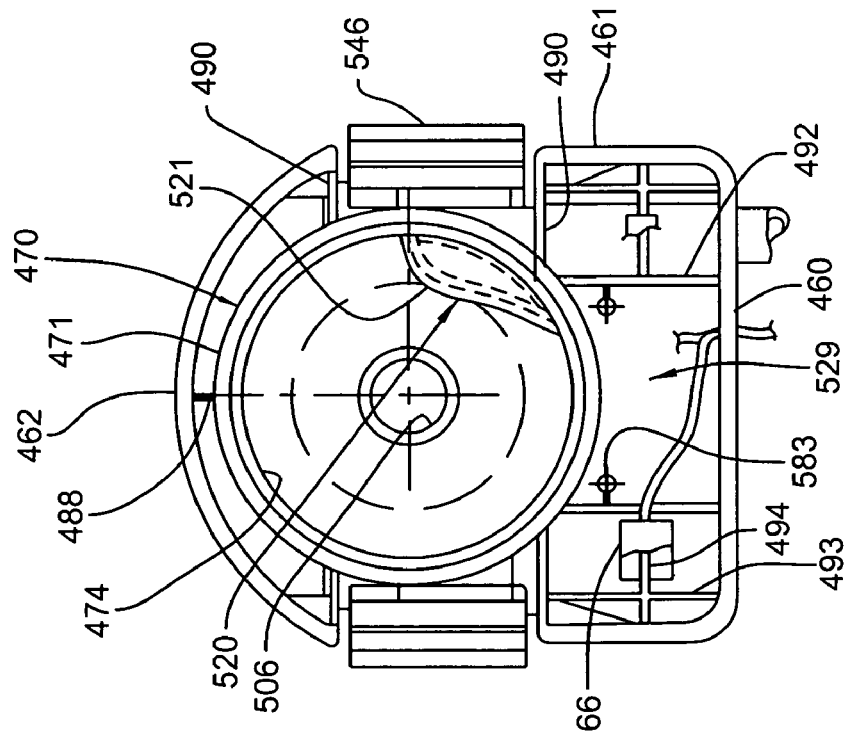
FIG. 23A is a front view of the FIG. 21 cassette body.
Figure 26:
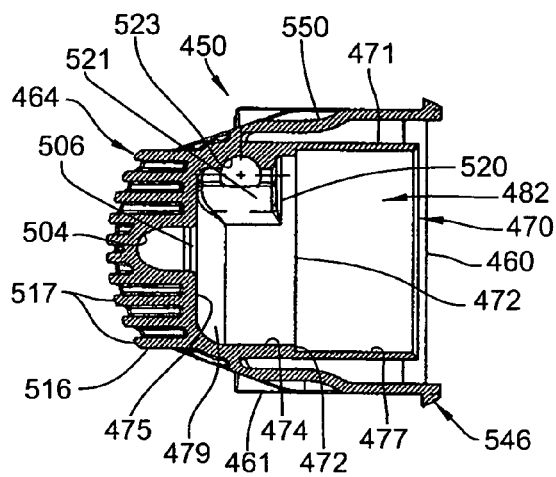
FIG. 26 is a cross sectional view substantially taken on the line 26-26 of FIG. 24.
Figure 24:
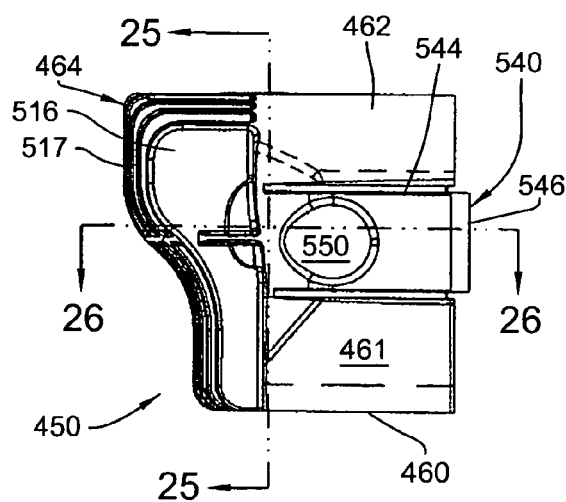
FIG. 24 is a right side view of the FIG. 21 cassette body.

The pump chamber peripheral wall 471 extends rearward from the cassette body front wall 464 almost to the rear end of the cassette body bottom, side, and top walls 460, 461 and 462, which extend rearward slightly therebeyond, as seen for example in FIGS. 21, 23, and 26. The pump chamber peripheral wall 471 is radially spaced somewhat from the cassette body side and top walls 461 and 462 and is fixed thereto by a radially upwardly extending, axially elongate fin 488 (FIG. 23A) and by laterally extending, axially elongate fins 490, respectively. The fins 490 comprise a substantially coplanar horizontal upper pair and a substantially coplanar horizontal extending lower pair, which pairs are spaced above and below the central axis of the pump chamber 470. The pump chamber peripheral wall 471 is substantially more greatly spaced above the cassette body bottom wall 460 and is braced with respect thereto by laterally spaced, vertically and axially extending fins 492 (FIGS. 23 and 23A). Additional stiffening, or reinforcing, fins may be provided as desired, for example as indicated at 493 and 494 in FIG. 23A.

The cassette body front wall 464 includes a forwardly thickened top portion 500 (FIG. 23). An irrigation liquid inlet recess 502 opens upward in the front wall top portion 500, is substantially of circular cylindrical form, has a preferably vertical central axis coplanar with the horizontal central axis of the pump chamber 470 and communicates with the front end of the pump chamber cavity 482 by means of a preferably right angle elbow passage 504. Preferably, a radially narrow, upward facing annular step 505 marks the joinder of the recess 502 to the top of the elbow passage 504. The lower, rear facing end of the elbow passage 504 is preferably coaxial with the central length axis of the pump chamber cavity 482 and defines the irrigation inlet port 506 thereto. The cassette body front wall 464, in its portion 510 below the elbow passage 504, extends downward and bends rearward in reduced cross section to follow the shape of the pump chamber front face 475 and fillet 479. Immediately below the pump chamber 470, and immediately forward of the fillet 479, the bottom portion 512 of the cassette body front wall 464 extends downward to the pump chamber bottom wall 460.

In the preferred embodiment shown, a plurality of closely laterally spaced, upstanding fins 516 extend forward from the cassette body front wall 464. The forward edges 517 of the fins 516 preferably follow a shallow S-curve which in turn generally follows the profile, seen in cross section in FIG. 23, of the irrigation liquid inlet recess 502 and elbow passage 504 and then drops down substantially vertically to the level of the cassette body bottom wall 460. As seen from above and below, (FIGS. 22 and 26), the forward edges 517 of the fins 516 collectively lie along a shallow, convexly rounded curve. The fins 516 collectively rigidify the front wall 464 of the cassette body, as well as providing a graceful decorative appearance.

Figure 25:
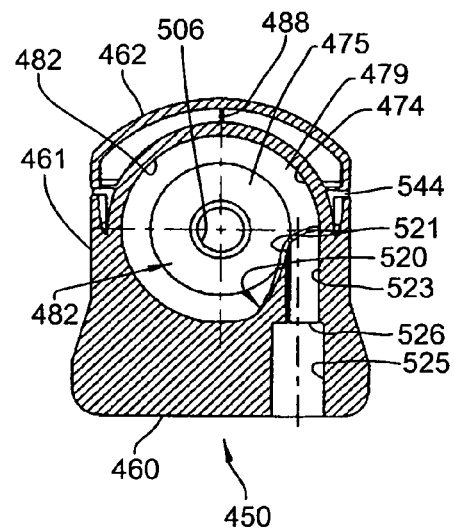
FIG. 25 is a cross sectional view substantially taken on the line 25-25 of FIG. 24.

A buttress 520 (FIGS. 23A, 25 and 26) is visible looking forward through the open rear end of the pump cavity 482. The buttress 520 extends upward from the bottom of the cavity and rearward from the front end face 475 of the pump chamber 470 along the rightward (in FIG. 25) side of the front inner peripheral surface 474 substantially to the level of the central length axis of the pump chamber 470. The buttress 520 extends rearwardly most of the axial length of the pump chamber rear inner peripheral surface but is spaced forwardly somewhat from the rear facing annular step 472. As seen from the front, in FIGS. 23A and 25, the laterally inboard face 521 of the buttress 520 is rounded in a gradual S-curve, for least interference with rotational irrigation liquid flow within the pump chamber 470, concavely from the bottom right portion of the front inner peripheral surface 474 upwardly and rightwardly convexly toward the rightward portion of the wall 477 substantially at the height of the longitudinal central axis of the cavity 482. As seen in FIG. 25, an irrigation liquid outlet passage 523 extends down through the top of the buttress 520 substantially flush with the front inner peripheral surface 474 of the pump cavity 482. A substantially circular cylindrical recess 525 opens downward through the bottom wall 460 of the cassette body 450 and joins the bottom of the outlet passage 523 at a downward facing generally annular step 526. As seen in FIG. 25, if may be convenient to slightly offset the axis of the passage 523 and recess 525. As seen in FIGS. 1 and 21, the irrigation liquid and outlet recesses 502 and 525 are configured to fixedly and sealingly receive the adjacent ends of the irrigation inflow and outlet tubes 44 and 46 in a generally conventional manner, with the ends of such tubes bottoming against the steps 505 (FIG. 23) and 526 (FIG. 25) to flow irrigation liquid into, and out of, the pump chamber cavity 482. It will be understood that in FIG. 25, pumped liquid flow will be clockwise for best flow past the buttress 520 and out through the outlet passage 523.

As schematically indicated in FIG. 23, a conventional annular seal, preferably a conventional O-ring 530 is sized to seat coaxially in the pump cavity 482 against the forward facing annular step 472 and the rearward inner peripheral surface 477, for purposes appearing hereinafter. A notch 528 (FIG. 22) opens through the cassette body bottom wall 460 and into the recess 525 for admitting the cable 64 (FIG. 1) into the interior of the cassette body 450, more particularly into a wiring chamber 529 (FIGS. 23 and 23A) beneath the pump chamber 470 and between laterally opposed ones of the fins 492.

The cassette body side walls 461 carry, and here incorporate, laterally opposed, rearwardly extending, generally rectangular, resiliently bendable, leaf-spring-like latch arms 540 (FIGS. 21, 23A, 24, and 26) having front ends 542 fixed, preferably integrally, on the side walls 461 adjacent the front wall 464. The latch arms 540 have elongate top and bottom edges separated from upper and lower parts of the sidewalls 461 by vertically spaced forwardly extending slots 544. The rear ends of the latch arms 540 carry vertically extended, laterally outwardly protruding, substantially triangular cross section (as seen in FIG. 26) fingers 546, each having a forwardly facing latch face 547 and a rearwardly and radially outwardly angled camming ramp 548. The rearward end of each latch arm 540, defined by its corresponding finger 546, extends rearwardly partially beyond the adjacent portions of the side walls 461 of the cassette body 450. Shallow, preferably textured finger/thumb depressions 550 face laterally outward from the latch arms 540 intermediate the front and rear ends thereof to facilitate manually pinching, and thereby bending, the rear portions of the latch arms 540 toward each other.

Laterally spaced guide pins 583 are fixed to extend rearward from the bottom portion 512 of the cassette body front wall 464 adjacent the lower portion of the pump chamber peripheral wall 471 (FIGS. 23 and 23A).

Turning now to the cassette cover subassembly 451 (FIGS. 21 and 27-31), same comprises a cassette cover 559 including a forward opening generally cup-like body 560 having a substantially closed front wall 562 and a circularly cylindrical peripheral wall 563 extending rearward from the front wall 562. An annular flange 564 extends radially outward from the front end of the peripheral wall 563.

The exterior surface 570 of the peripheral wall 563 is substantially cylindrical, except for a front facing annular step 571 adjacent the front end of the body 560 (FIG. 31) leading to a reduced diameter, substantially cylindrical boss 572.

A cylindrical stub 576 (FIG. 31) protrudes coaxially rearwardly from the front wall 562 to approximately half the depth of the rear opening interior chamber 577 of the cup-like body 560. The inner peripheral surface 578 of the peripheral wall 563 is tapered in a rearwardly divergent manner at an angle A3 substantially equal to the angle A2 (FIG. 11) of the exterior annular surface 109 of the tubular shell 100. The inner peripheral surface 578 is annularly rounded at its rear end to form a bell mouth 588.

Evenly circumferentially spaced, stiffening webs 580 (FIGS. 29-31), here four in number, extend radially from the stub 576 outward to the body peripheral wall 563 and rearwardly from the body front wall 562 nearly to the rear end of the stub 576. The stub 576 includes a central through bore 584 coaxial with the stub 576 and at the cup-like body peripheral wall 563. A coaxial cylindrical recess 585 opens rearward from the central bore 584, toward the open rear end of the cup-like body 560.

The radially outwardly extending flange 564 (FIGS. 29 and 30) has a convexly rounded top edge 590, laterally spaced upstanding side edges 591 and a laterally extending bottom edge 592. Shallow, generally rectangular, laterally outward opening, vertically elongate, notches 595 (FIGS. 30 and 31) are formed in the upstanding side edges 591 at the ends of the top edge 590 and have upper portions flanking the central length axis of the cylindrical stub 576.

A recess 600 (FIGS. 28 and 31), here of generally circular shape, opens rearwardly from the flange 564, here below the peripheral wall 563 of the cup-like body 560, and fixedly houses a shallow, cylindrical, substantially puck-like permanent magnet 601. The rear wall 603 of the recess 600 is sufficiently thin (e.g. 0.050 inch or so) that the magnetic field of the magnet 601 extends, with only minor reduction, rearward from the flange 564. The magnet 601 and sensor 136 act as the system-on switch as hereafter discussed.

A pair of hollow, preferably cylindrical, tubular projections 608 (FIGS. 28 and 31) extend forwardly from the front face of the flange 564 in close spaced proximity beneath the peripheral wall 563 of the cup-like body 560, and in laterally spaced flanking relation with the recess 600.

Figures 27, 28:
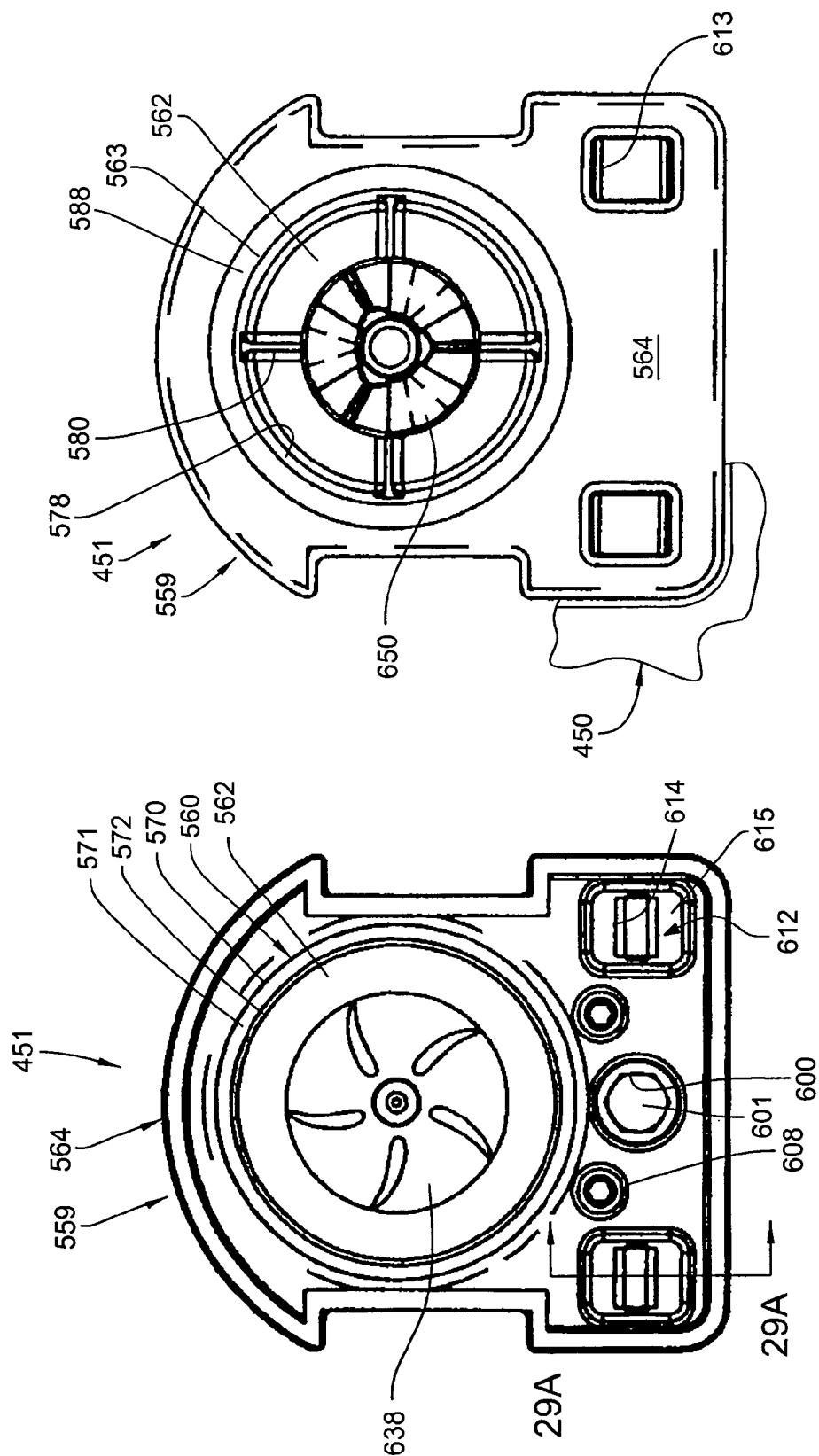
FIG. 27 is a rear view of the cassette cover subassembly of FIG. 21.
FIG. 28 is a front view of the FIG. 27 cassette cover subassembly.

Generally rectilinear, box-like bosses 612 protrude slightly forwardly from the lower corner portions of the flange 564, are generally vertically centered on and wide spaced laterally on opposite sides of the magnet 601, and have upper portions more closely spaced upward from and flanking the tubular protrusions 608. The box-like bosses 612 open rearwardly from the flange 564, to form respective rearward opening, generally rectilinear wells 613 (FIG. 27). Horizontally elongate, generally rectangular slots 614 (FIG. 28) open through the vertical midportion of the otherwise closed front end wall 650 of each of the bosses 612.

Electrically conductive, resilient contacts 620 (FIGS. 29 and 29A) of generally arrow-head profile, each comprise a generally keyhole shaped central opening 621 having a widened rear portion and narrowed front portion. The contact 620 has a relatively wide, convexly rounded rear portion, and tapers to a narrowed front portion 625. The contact 620 has oppositely facing outward opening grooves 628 immediately behind the narrowed front portion 625, to the immediate rear of which lips 630 angle forwardly and oppositely outwardly. The resilient, rubber-like material of the contacts 620 enables same to flex but is also electrically conductive, to enable it to conduct electrical current, by reason of incorporated contiguous conductive particulate matter not shown. The contact 620 is conveniently formed by extrusion followed by cutting into desired length segments, as will be clear from FIG. 29. While the contact 620 may be formed of various materials having the characteristics above mentioned, one such material is a rubber material loaded with nickel/graphite so as to be conductive, and available from Laird Technologies, located at San Jose, Calif.

The contacts 620 are installed in the flange 564 of the cassette cover 559, in respective ones of the wells 613. More particularly, the narrowed front portion 625 of each contact 620 is inserted forwardly into its corresponding well 613 and snap fitted through the corresponding slot 614 in the front end wall 615 of the corresponding boss 612, such that the top and bottom edges of the slot 614 are received in the grooves 628 of the contact 620 and retained therein to block rearward escape of the contact 620. The contact lips 630 lie in the well 613 and resiliently bear against the front end wall 615 of the boss 612 to block further movement of the contact 620 with respect to the boss end wall 615. The widened rear portion 624 of the contact 620 extends rearwardly slightly beyond the rear face of the flange 564 to resiliently and electrically engage the slightly protruding front head of the pin-like console face plate contact 168, which aligns therewith, in the assembled FIG. 2 apparatus.

A conventional, generally C-section conductive terminal 66 (FIG. 29, 29A) is conductively fixed on the adjacent end of each of the insulated wires 65 defining the cable 64. This concave side of each terminal 66 is pressed fixedly onto the front edge of the right and left horizontal fins 494 of FIG. 23A. Thus, with each contact 620 in its installed FIG. 29A position in its boss 612, its narrow front portion 625 resiliently and electrically conductively presses against the corresponding conductive terminal 66, to electrically connect the wires of cable 64 to the resilient contacts 620.

A shaft 636 (FIG. 29) is rotatably received in the central through bore 584 and protrudes forwardly and rearwardly therebeyond. The thus exposed front end of the shaft 636 fixedly and coaxially carries a pump impeller 638 (FIG. 29), having a radially extending base 639 and liquid engaging and impelling blades 640. To the extent described, the impeller 638 may be similar to that disclosed in U.S. Pat. No. 5,484,402 assigned to the assignee of the present invention, the disclosure which is incorporated by reference herein. The impeller 638 further includes a radially buttressed, rearward extending spacer hub 641 for bearing rotatably on the front wall 562 (FIG. 31) of the cassette cover 559.

The exposed rear portion of the shaft 636 carries, in sequence, an annular seal (preferably an O-ring) 644 for bearing against the rear end of the stub 576 (FIG. 31) in liquid sealing relation, a conventional jamb washer 646 for fixedly retaining the O-ring 644 against the stub 576, a disk-like coupler adaptor 648, and a cassette coupler 650.

The coupler adaptor 648 comprises (1) a disk 660, (2) a hub 661 fixedly and coaxially extending rearward from the disk, (3) evenly circumferentially spaced, generally rectangular, outward opening, perimeter notches 664 (here three in number), and (4) forwardly extending pins 666 fixed to the rear face of the disk 660 in evenly circumferentially spaced relation with each other and with the notches 664 and equally spaced between the hub and the peripheral edge of the disk 660. The disk 660 is washer-like, with a central opening (not shown) to receive the rear end portion of the shaft 636 rearwardly therethrough. The hub is hollow with a central through opening communicating with the central opening of the disk in a coaxial manner and receiving the rearward portion of the shaft 636 therethrough.

The cassette coupler 650 (FIGS. 33-33B) comprises a disk-like base 670 and a rearward extending hub 672. Equally circumferentially spaced, driven teeth 674 (here three in number) extend rearwardly from the base 670 and beyond the hub 672. The teeth extend radially outward from the hub substantially to the periphery of the base 670. The radially outer surfaces 675 of the teeth are rearward extensions of the peripheral edge of the circular disk-like base 670, and hence may be thought of circumferentially spaced segments of a circular cylinder. The circumferentially spaced sides 677 of each tooth 674 lie in planes extending rearwardly and toward the longitudinal axis of the shaft 636 and hub 672, as seen in FIG. 33B, at an angle A6 preferably in the range 57-63 degrees, here 60 degrees.

In the embodiments shown, the portions of the tooth sides 677, immediately adjacent the base 670, are preferably filleted, as indicated at 678, into the base 670 to strengthen the connection of the teeth to the base. The free, rear ends of the teeth 674 are pointed in profile, looking radially inward at the center tooth 674 in FIG. 33, as defined by rearwardly convergent and upwardly convergent (in FIG. 33), planar ramp, or guide, faces 680 meeting with their rearward edges in a radially extending ridge line 681. Each tooth 674 has a radially inboard face 684 (FIG. 33A) angled rearward and somewhat radially outward from the rear end of the hub 672 at an angle A5 (for example in a range of 100 to 105 degrees, here about 102 degrees).

The cassette coupler 650 has a cylindrical, coaxial, forwardly chamfered bore 688 sized to fixedly snugly receive the hub 661 of the coupler adaptor 648 (FIG. 29), as by press fit or other convenient fixed securement. The cassette coupler 650 further includes forward opening, cylindrical, forwardly chamfered drive pin recesses 690 preferably circumferentially centered at the base of each tooth 674, the pin recesses 690 being sized and located to snugly drivingly receive the pins 666 of the couple adaptor 648 for circumferential driving of the coupler adaptor 648, shaft 636 and impeller 638 by the cassette coupler 650.

The cassette coupler 650 is preferably of a relatively stiff, somewhat resilient, rubber-like material (for example a material available under the trade name SANTOPRENE™ model 201-73, available from Advanced Elastomer Systems located at Akron, Ohio. This material has surface resilience to accommodate some misalignment between the cassette coupler 650 and the motor coupler 158 (FIG. 9), as well as to damp noise of contact therebetween as the motor 144 turns on and off and torque applied by the coupler 158 to the coupler 650 reverses.

The motor coupler 158 (FIG. 32) is generally similar in appearance to the cassette coupler 650 but differs therefrom in several respects as follows. The motor coupler 158 has teeth 704 which differ in size and shape from the teeth 674 so as to axially and circumferentially drivably receive in the circumferential spaces 703 therebetween the driven teeth 674 of the cassette coupler 650.

The angle A7 defined by the circumferentially oppositely facing side 706 of each tooth 704 is preferably in the range 77 to 81 degrees, here 79 degrees. The sides 706 of a given tooth 704 lie in planes converging toward the hub 708 of the motor coupler 158 and meet on an axial line through the adjacent radially outer portion of the hub 708 and spaced radially outward from the central axis of the hub 708 and motor coupler 158. The angle A8 defined circumferentially across the space 703 between adjacent teeth 704 is preferably in the range of 38 to 44 degrees, here 41 degrees, and the planes of the thus spaced tooth sides 706 extend inward past the hub 708, here substantially to the radially inboard end of the ridge 710 of the diametrically opposed tooth 704. In any event, the radially outer portion 707 of each tooth 704 of the motor coupler 158 fits snugly circumferentially between the radially outer portions of two teeth 674 of the cassette coupler 650, and vice versa, as indicated in dotted lines at 674 in FIG. 32A and 704 in FIG. 33B, to transmit torque at the outer perimeter portions of the couplers.

The motor coupler 158 has a rearward (downward in FIG. 32) opening, blind bore 712 for receiving and fixedly (by any convenient means not shown) engaging the front end of the motor shaft 146 (FIG. 9). The motor coupler 158 is sized to fit rotatably within the forward facing recess 107 (FIG. 11) of the front chassis 80 and is preferably of a diameter substantially identical to that of the cassette coupler 650. The motor coupler 158 (FIG. 32) lacks the pin recesses 690 of the cassette coupler 650 and is preferably of a hard, rigid material, such as, for example, anodized aluminum. Otherwise the motor coupler 158 is generally similar to the cassette coupler 650 above described in more detail.

Figure 29:
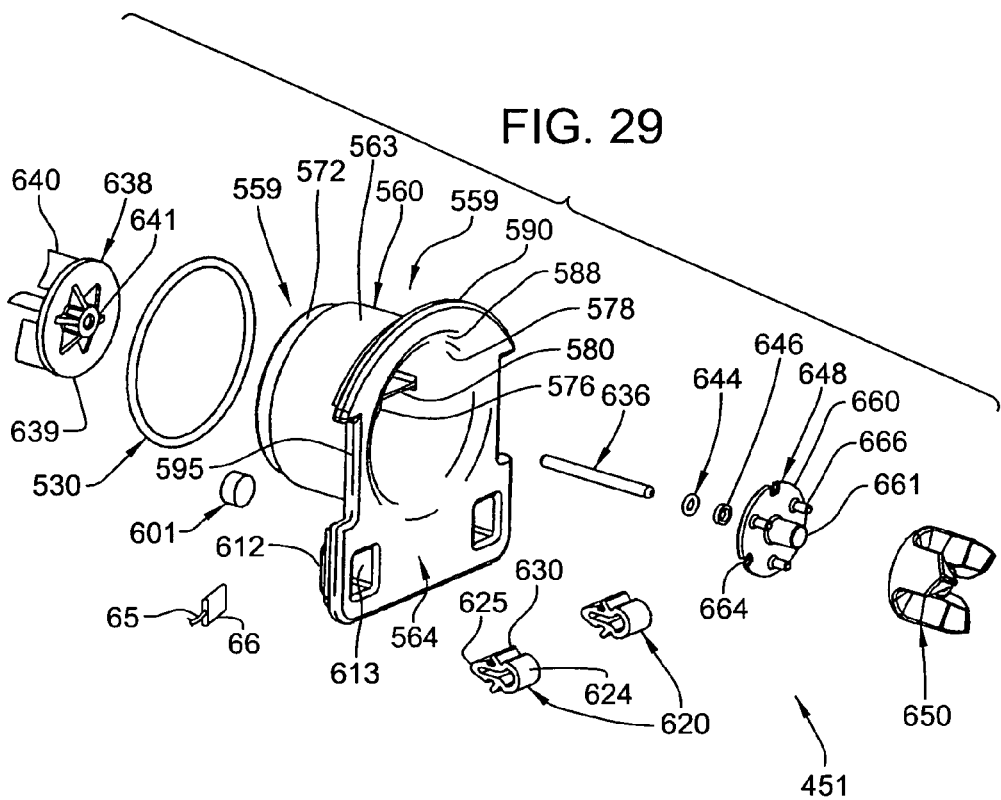
FIG. 29 is an exploded pictorial view of the cassette cover subassembly of FIG. 21.

The major parts of the apparatus are of complex form and are conveniently and economically of molded plastics materials. See for example, parts 180, 158, 80 and 194 (FIG. 9), parts 400, 250, 300 and 385 (FIG. 15) and 650, 451, 450, and 638 (FIG. 21), and part 648 (FIG. 29).

The above described control 180 (FIG. 9) and power supply 384 (FIG. 15) may be conventional and of any convenient type. It is preferred that the circuitry of the apparatus be as block diagramed in FIG. 34, with a control 180 in the form of a suitably programmed microcontroller operating as described hereafter. However, it is also contemplated that the fundamental operation of the apparatus could be controlled manually as hereafter discussed with respect to FIG. 34A.

Figure 34:
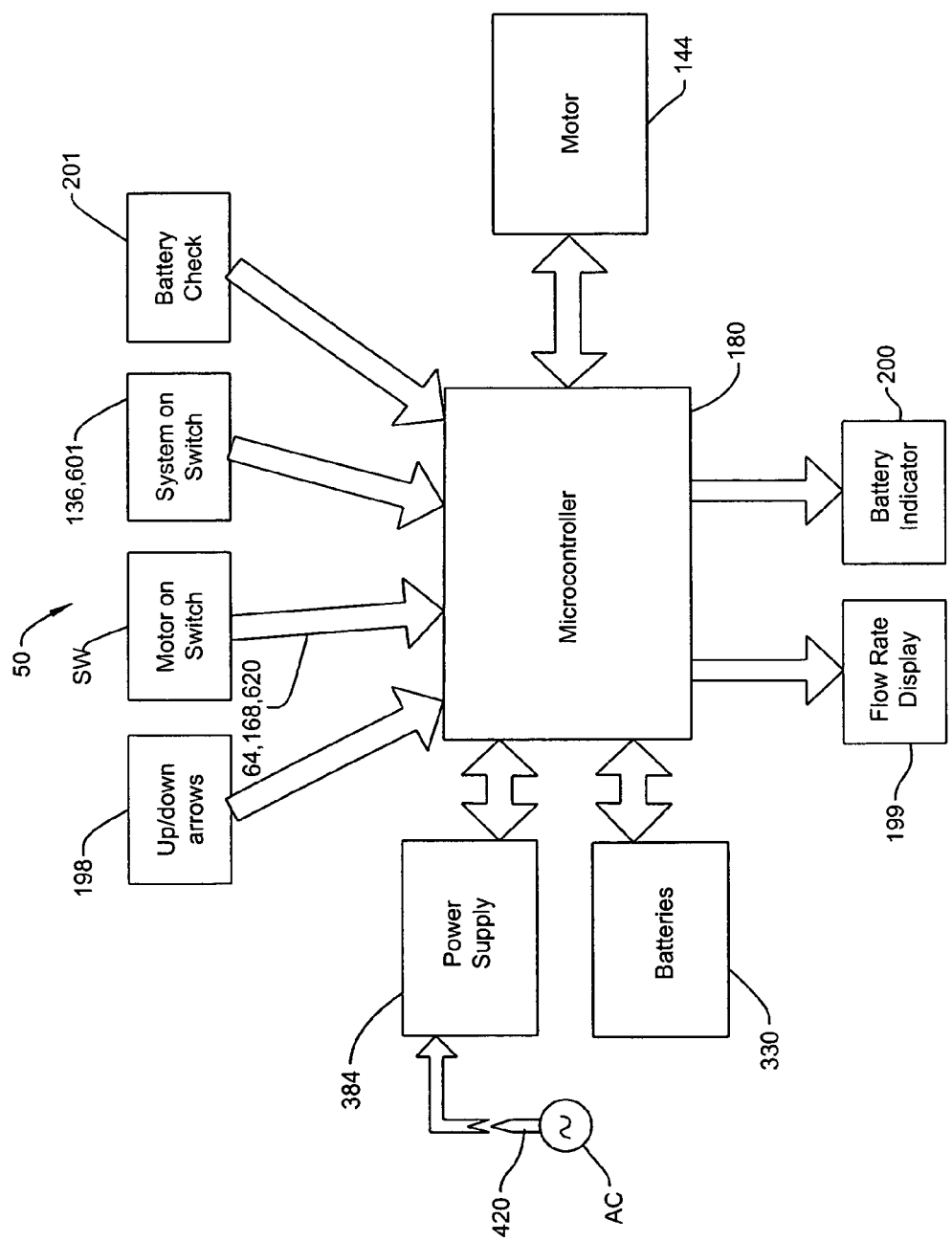
FIG. 34 is a schematic block diagram of the operating circuitry of the FIG. 1 system.
Figure 34A:
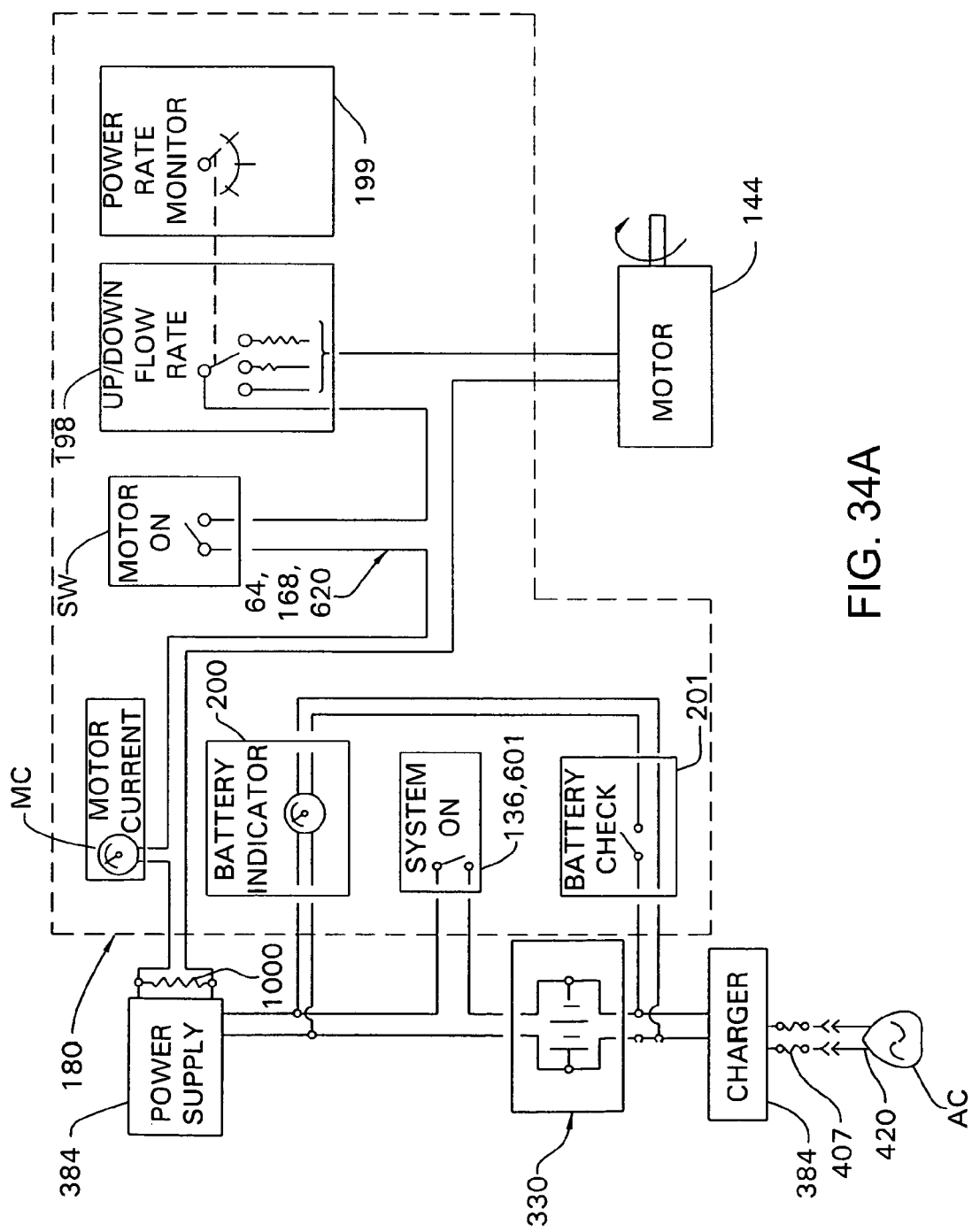
FIG. 34A is a schematic diagram of a simplified control for the FIG. 1 system.

Thus, the FIGS. 34 and 34A embodiments provide for temporary connection of the AC source AC through the power cord 420 to the power supply unit 384 to charge the batteries 330 (in FIG. 34 by a path through the microcontroller 180). The battery unit 330 provides electrical operating power to the control 180. The motor on/off switch SW of the handpiece 50, the system turn on switch defined by the contacts 136 and 601, the battery check switch 201 and the flow rate control switch 198 are manually responsive and provide controlled inputs to the control 180 which provides the outputs to the flow rate display 199 and battery status indicator 200, as well as having a monitorable electric current output path to the motor 401.

Assembly

Assuming the console 14 to be assembled in the manner above discussed and the cassette unit 16 to be assembled in the manner above discussed, including the handpiece 50 and the tubes variously indicated at 44, 42, 46 and 60, the power cord 420 is connected to the conventional AC source AC (e.g. a conventional 120 VAC wall socket) and to the power entry module 400 (FIGS. 1 and 15) in the back of the rear console assembly 71 of the console 14, to charge the battery pack 330. The battery indicator 200 can be connected to indicate battery condition by reason of (1) the system on switch 136, 601 connecting the battery pack 330 to the power supply 384 or (2) upon activation of the battery check switch 201 or (3) during charging in the FIG. 34 embodiment, or more simply in the (2) and (3) conditions in the simplified FIG. 34A embodiment.

With the battery pack 330 fully charged, power cord 420 may be disconnected and the surgical irrigation apparatus 12 (FIG. 1) is ready for use.

Figure 20:
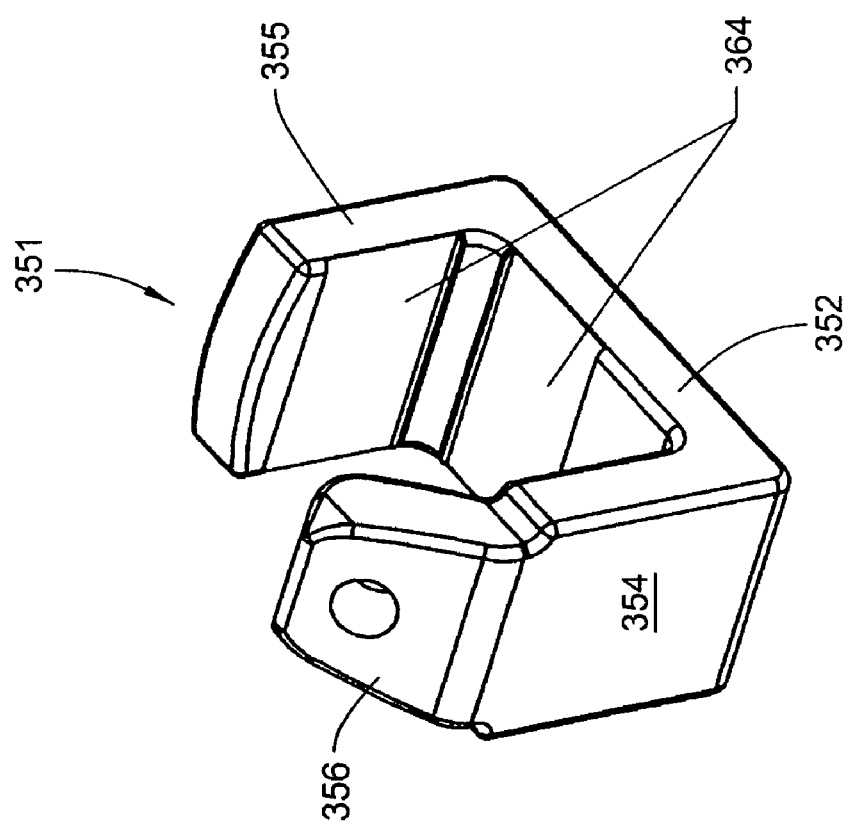
FIG. 20 is a pictorial view of the clamp of FIG. 15.

To ready the apparatus for surgery, the console 14 is fixed to a support (e.g. the FIG. 1 pole 22) as shown in FIG. 3, namely by pocketing the pole 22 against the friction pads 364 (FIG. 20) of the clamp base 351 and tightening the clamp screw 360 (FIGS. 3 and 5) to fix the pole 22 against the clamp base 351 at a convenient height on the pole 22.

The cassette unit 16 is prepared as schematically indicated in FIG. 1, namely with irrigation inlet tubes 42 and 44 running to the inlet of the pump cassette 40 and irrigation outlet tube 46 and cable 64 running from the pump cassette to the handpiece 50 and with the handpiece connected by the suction tube 60 to a suction container SC in turn connected to a suitable suction terminal ST and with a tip 58 of desired type fixed to the front end of the handpiece 50. The arrangement of the handpiece 50 tubes 46 and 60, cable 64 and tip 58 is preferably similar to that disclosed in the prior U.S. patents above mentioned and assigned to the assignee of the present invention.

With an irrigation liquid bag, or bags, 25, on the arms 23 (FIG. 1) on the pole 22, and spaced above the console 14, a conventional inlet fitting, sometimes referred to as a spike, 30 (FIG. 21), with its usual protective cover 31 removed and its bottom portion 32 connected to the upper end of the tube 42 or 44 (FIG. 1), is inserted upward into the outlet fitting 27 of a corresponding irrigation liquid bag 25.

The pump cassette 40 can depend from its thus connected tube 42 adjacent the console 14 until it is to be used by the surgical team. At that point a surgical team member grips the pump cassette 40 from the front (seen in FIG. 2) thereof and pushes the rear portion of the cassette 40 into the front opening cassette main recess 96 (FIG. 9). Continuing, the front ends 542 (FIG. 21) of the cassette latch arms 540 enter the slots 103 (FIGS. 2D, 7 and 10) on opposite sides of the back wall 98 of the cassette receiving recess 96 of the front console chassis 80, the feet 546 resiliently engaging and sliding rearward along the upward walls of the slots 103 and finally snapping resiliently laterally outward so as to be trapped snugly behind the cassette mounting bezels 102 (FIGS. 2D and 10). At the same time, the rear portion of the assembled cassette body 450 and cassette cover subassembly 451 (FIG.

Figure 2B:
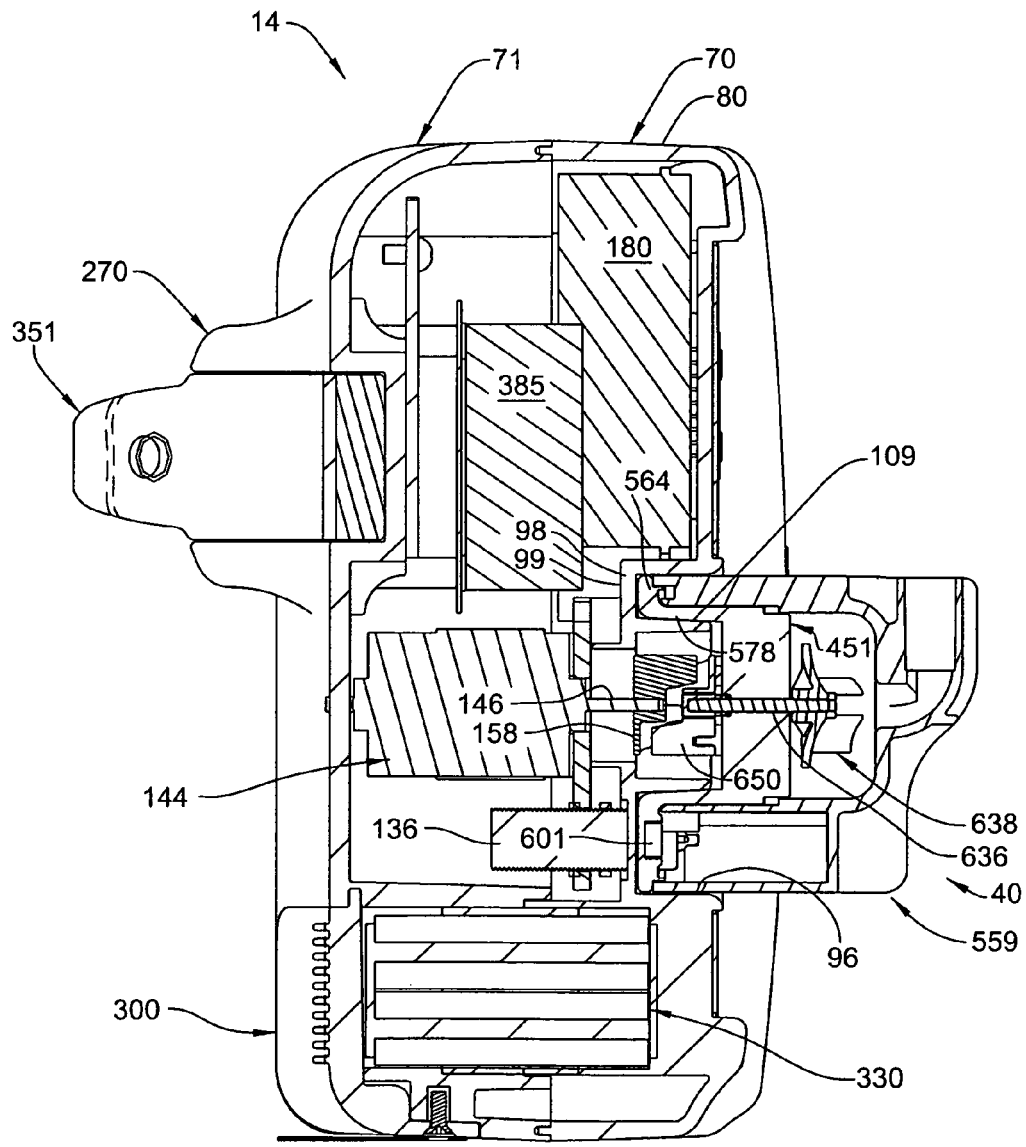
FIG. 2B is a central cross sectional view substantially taken on the line 2B-2B of FIG. 2A.
Figure 2C:
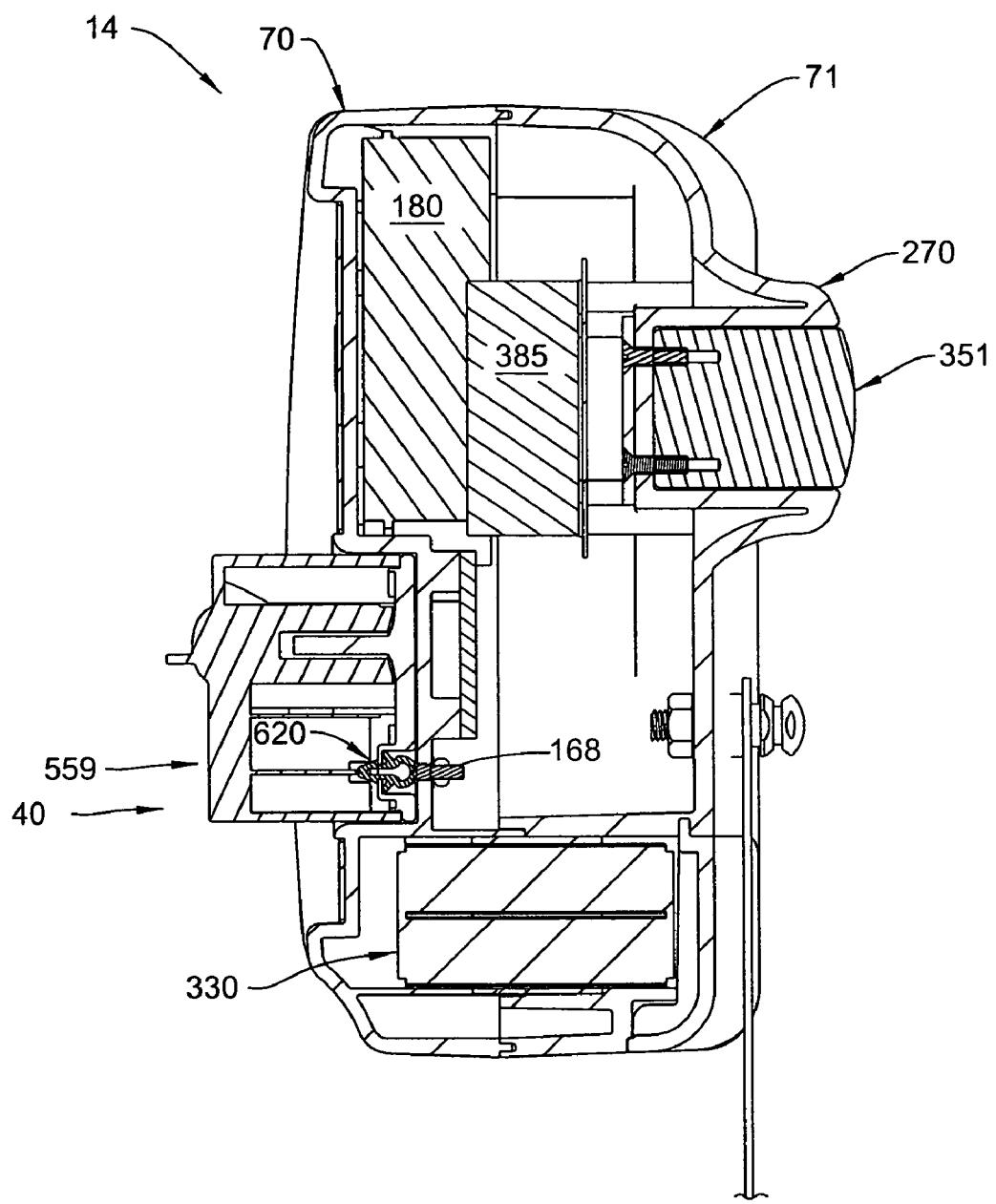
FIG. 2C is a cross sectional view substantially taken on the line 2C-2C of FIG. 2A.
Figure 2D:
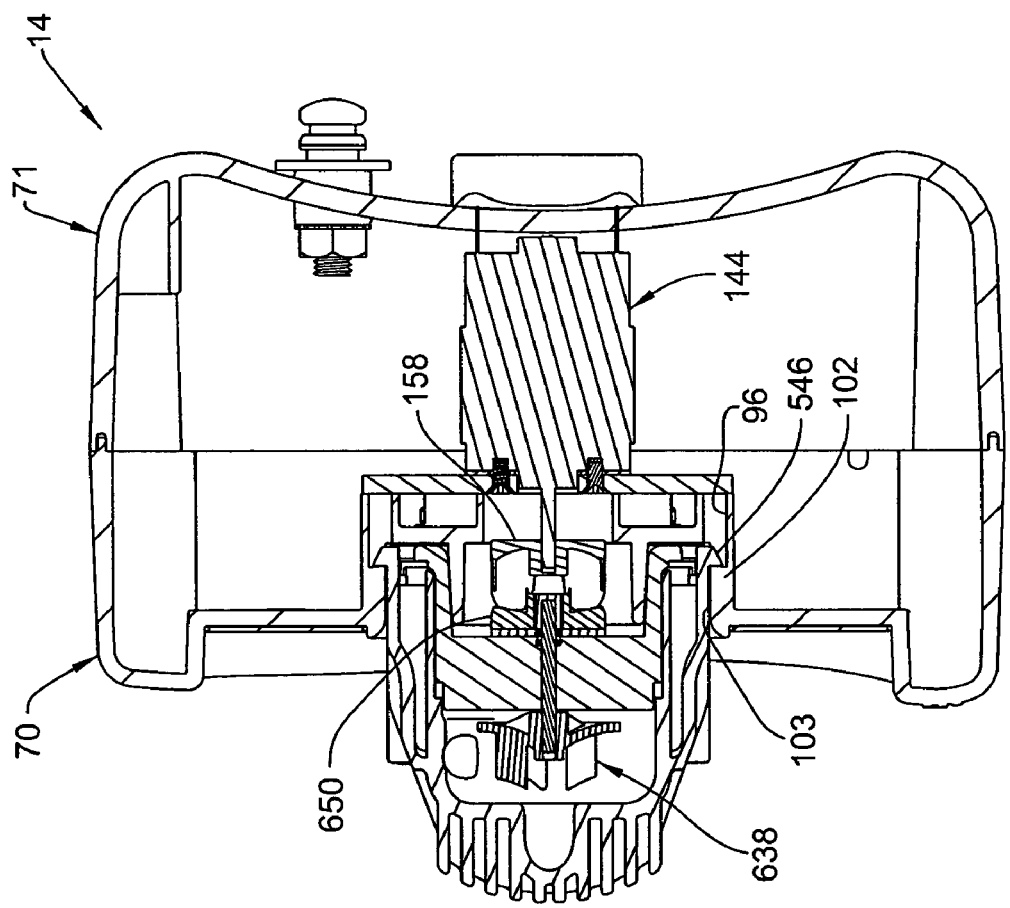
FIG. 2D is a cross sectional view substantially taken on the line 2D-2D of FIG. 2A.

21) enters rearwardly into the open front of the cassette receiving recess 96 (FIG. 11) and into the fully installed position of FIGS. 2B and 2D. In this position, the forwardly convergently tapering, external annular surface 109 of the front console chassis 80 has snugly telescopingly entered into surrounded, contacting relation with the rearwardly divergently tapered annular inner-peripheral surface 578 of the cassette cover subassembly 451 (FIGS. 2B and 29A), thereby precisely coaxially locating the motor shaft 146 and impellor shaft 636. This brings the motor coupler 158 and cassette coupler 650 (FIGS. 32 and 33) coaxially together, the ramps 709 and 680 thereof slidingly, cammingly engaging to interdigitate the teeth of each coupler 158 and 650 in the between-tooth spaces of the other, in circumferentially snug, rotatably driving engagement.

Further, such pushing of the pump cassette 40 into the front recess portion of the front chassis 80, places the rear cassette flange 564 (FIGS. 2B and 21) into snug engagement with the front face of the back wall 98 (FIGS. 2B and 11) of the boss 99.

This places the magnet 601 (FIG. 2B) into coaxially opposed activating relation with the magnetic proximity sensor 136 and brings the resilient contacts 620 (FIGS. 2C and 29A), which in turn are electrically connected to the insulated wires of the cable 64 leading to the switch SW on the handpiece 50, into resilient contact with and electrically conducting relation with the pin-like console face plate contacts 168 of the front console assembly 70.

With the cassette unit 16 fixed to the front of the console 14, as above discussed with respect to FIGS. 2A-2D, the batteries 330 energize the flow rate display 199 and battery indicator 200, directly as seen in FIG. 34A or through the microcontroller 180 as seen in FIG. 34.

Thereafter, closing the switch SW on the handpiece 50 (FIG. 1), here by pushing the irrigation trumpet valve push button 54, completes the electrical path through the wires of the cable 64 (FIGS. 1 and 2) and thence through the terminals 66 on the cable wires 65 (FIG. 29A) to the resilient electrical contacts 620 in the flange 564 of the cassette cover 559 (FIGS. 2C, 21, 29, and 29A), and hence through the pin-like console face plate contacts 168 (see also FIGS. 4, 7, 8, 9, and 12) to complete the electric current path to the motor 144 directly as seen in FIG. 34A or through the microcontroller 180 as in FIG. 34. This turns on the motor 144 which rotates the couplers 158 and 650 (FIGS. 2B, 2D, 7, 9, 21, 27, 29A, 32 and 33) and thereby the pump impellor 638 (FIGS. 2B, 2D, 21, 28, and 29). The impellor 638 thereby pumps the irrigation liquid, incoming through the irrigation liquid inlet recess 502 (FIG. 23) and elbow passage 504 and inlet port 506, clockwise as seen in FIG. 25 and thence down through the irrigation liquid outlet passage 523 in the buttress 520 and into the outlet tube 46 (FIG. 1) received in the recess 525 of FIG. 25 to the handpiece 50. Pumped liquid from the tube 46 thus passes through the handpiece irrigation valve opened by depression of the valve push button 54, as above described, to flow irrigation liquid through the handpiece tip 58 to the surgical site SS of the patient P.

In the foregoing, with the inlet tube 42 (directly or through the Y tube 44) spiked into the irrigation liquid bag 25 (FIG. 1) the cassette 40 hangs directly in front of the console 14, and specifically in front of the cassette recess 96. Thus, a surgical team member need only push the cassette rearward, in a single movement, to insert the cassette into the console. This "single-movement" insertion is further made possible by the horizontal orientation of the pump impellor shaft 636 (FIG. 2B) and motor shaft 146.

Further, the matching conical tapers of the walls 109 and 578 (FIG. 2B) of the console 14 and cassette 40, surrounding the engaged couplers 158 and 650, and the reception of the console's conical protrusion (or substantially tubular shell) 100 in the corresponding tapered conical hole (defined by the inner-peripheral surface 578 of an interior chamber 577 of the cup-like body 560 of the cassette cover 559) (FIGS. 29 and 31), properly aligns the cassette in the console and allows for as tight a fit as possible therebetween for efficient power transmission from the console to the cassette. This conical fit feature allows the cassette to easily slide into position until, when fully in position, tight tolerances ensure proper supporting fit of cassette on console and coaxial alignment of the motor and impellor shafts.

Further, it is the installation of the cassette 40 on the console 14 that causes the magnet 601 (FIG. 2B) to actuate the sensor 136 (preferably a conventional reed switch) to automatically connect the battery pack 330 to the control 180 (FIGS. 34 and 34A) to automatically "power up" the console 14. This saves the user the usual additional step of separately turning on the system by pushing a start button or the like, as in conventional systems.

Further, providing one of the couplers 158 and 650, preferably the cassette coupler 650, of a flexible rubber, or rubber-like plastic, material enables efficient power transmission from the motor to the impellor despite possible misalignment of the motor and impeller shafts.

Figure 29A:
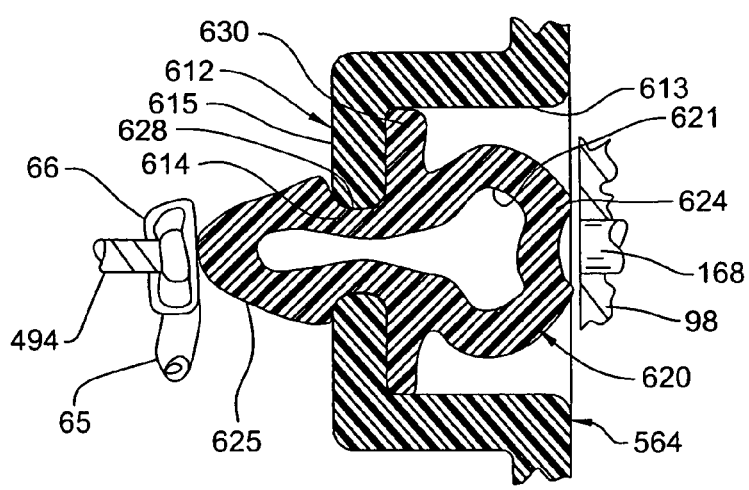
FIG. 29A is a cross sectional view substantially taken on the line 29A-29A of FIG. 28 and including assembled components of the cassette body 450 and cassette cover subassembly 451.
Figure 30:
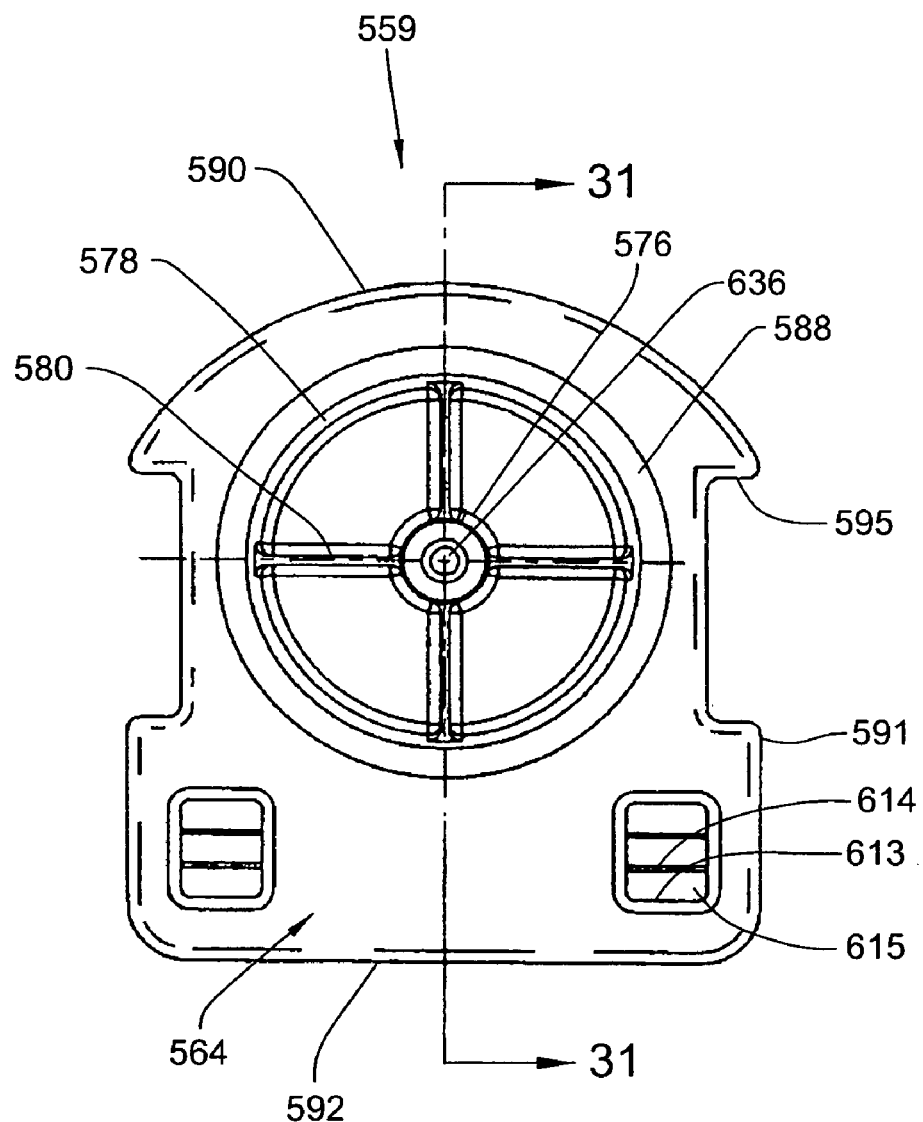
FIG. 30 is a front view of the cassette cover of FIG. 29.
Figure 31:
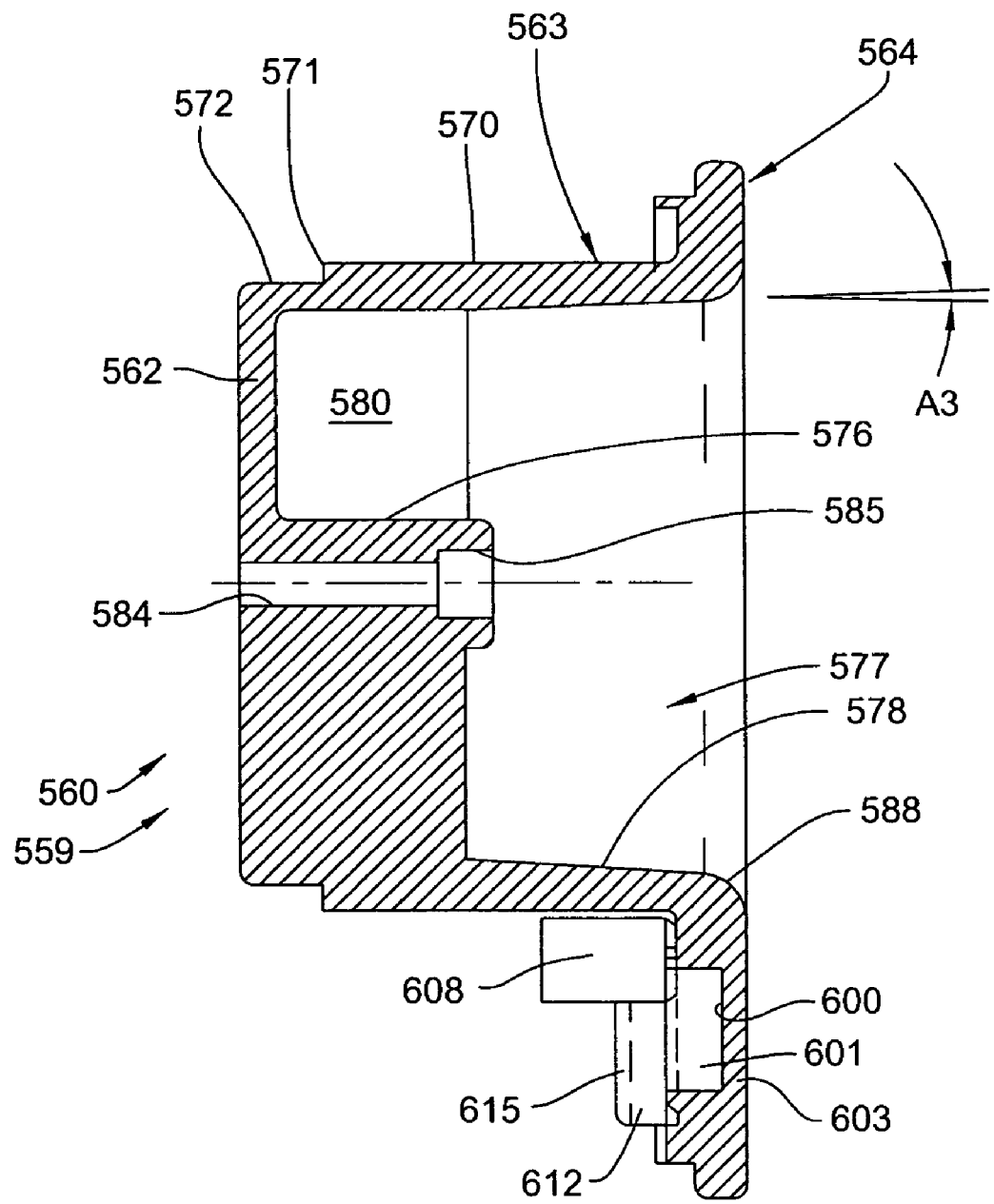
FIG. 31 is a central cross sectional view substantially taken on the line 31-31 of FIG. 30, with the upper one of the radial webs shown in relief.

Further, the provision of electrical connection between the cassette and console in the form of the rubber, or rubber-like plastic, electro-conductive contacts 620 (FIGS. 2C, 21, 29, and 29A), set into the flange 564 of the cassette cover 559, provides a clean looking and flexible method for transmitting the electrical signal (switch SW closure) from the handpiece 50 through the cassette 40 to the console 14. The resilience of the contacts 620 establishes reliable and full electrical contact with the pin-like contacts 168 of the console (as schematically indicated in FIG. 29A) despite variation in the clearance between the cassette flange 564 and the back wall 98 of the recess 96 of the console 14.

Further, electrically powering the console 14 with a battery (onboard battery pack 330) reduces clutter in the surgical operating room by eliminating the usual AC power cord which typically powers conventional irrigation supply consoles. Further, the battery pack 330 is sized to provide operating power for a number of typical operations (e.g. 30). Moreover, construction of the battery pack 330 from rechargeable cells and inclusion of means in the console 14 to recharge the battery pack 330 (usually outside the surgical operating theater between surgical operations) essentially eliminates the time and effort required to change batteries over the life of, or at least infrequently during the life of, the console 14, for significant labor cost savings and eliminates frequent battery cell purchases.

Further, the buttress 520 (FIG. 25) protruding into the volute (i.e. the front inner peripheral surface 474) of the pump chamber 470, raises the chamber outlet to the irrigation liquid outlet passage 523 vertically, substantially to the horizontal diametral plane of the pump chamber 470. Thus, initial gravity flow, from the irrigation liquid supply bag 25 through the tube 42 (FIG. 1) into the pump chamber 470, quickly fills the pump chamber over half full, namely up to the level of the impeller axis and reliably primes the pump, yet allows the cassette body 450 to be molded as a single piece. Applicants found that locating the irrigation liquid outlet lower in the pump chamber interfered with reliable priming.

Preferably, the mechanical self priming and mentioned method are used together to ensure proper priming.

Figure 35:
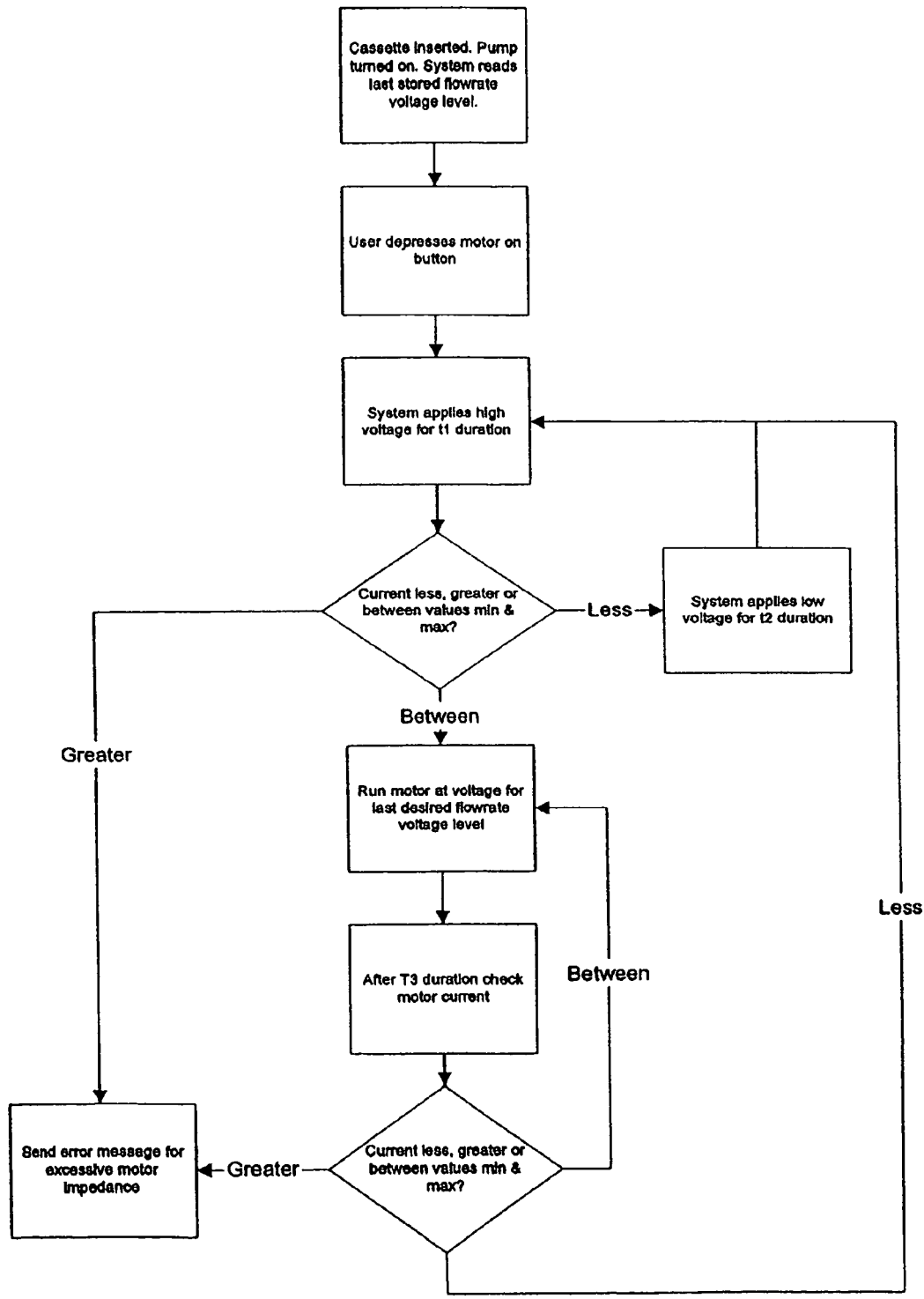
FIG. 35 is a flowchart of a method for priming the pump, either manually or by means of the FIG. 34 control.

In addition to this mechanical self priming of the pump, an embodiment of the invention provides a method for checking and assuring priming of the pump, which method can be carried out manually, using the FIG. 34A embodiment, or conveniently, by appropriate programming of the FIG. 34 microcontroller 180, such method being set forth in the FIG. 35 flowchart.

Attention is directed to the priming flowchart of FIG. 35. As above indicated, insertion of the cassette 16 into the console 14 closes the contacts 136, 601 and 30 automatically turns on the system 10. The system 10 thus is ready to proceed at the last voltage level set (stored) by the up-down flow rate switch 198. To turn on the pump motor, the user depresses the irrigation valve button 54 on the handpiece 50, thereby closing the motor-on switch SW (FIGS. 34 and 34A). The microcontroller 180 (or the user in the FIG. 34A embodiment by using the up-down flow rates switch 198) applies maximum voltage to the pump motor for a predetermined time duration T1. If motor current sensed by the FIG. 34 microcontroller (or seen by the user in the FIG. 34A embodiment on the motor current readout MC) is within a desired range, between minimum and maximum, the motor is run by the FIG. 34 microcontroller at the first mentioned "stored" flow rate voltage level or, in the case of the FIG. 34A manual embodiment, by the user resetting the up-down flow rate switch 198. If motor current sensed by the FIG. 34 microcontroller (or seen by the user in the FIG. 34A embodiment on the monitor current read out MC) is above the desired range, the motor impedance is excessive and an "error" situation exists. On the other hand, if motor current is less than the desired range minimum, the microcontroller of FIG. 34 (or the user in the FIG. 34A system using the up down flow rate switch 198) switches the motor voltage low for duration T2. Then the maximum voltage is applied to T1 duration. Next, the motor current is again monitored. If motor current is in the desired range, the motor is run by the FIG. 34 microcontroller at the first mentioned "stored" flow rate voltage level (or, in the case of the FIG. 34A manual embodiment, by the user resetting the up-down flow rate switch 198.

After a time T3, motor current is checked again to determine if it is less than, greater than, or in the desired range. If greater, the above described error condition exists. If less, the microcontroller of FIG. 34 (or the user in the FIG. 34A embodiment) once again applies high voltage for the T1 duration and the cycle following the third step of the FIG. 35 flow chart starts again. If in the desired range, the motor continues to receive the last desired flow rate voltage level, namely per step 5 of the FIG. 35 flowchart.

Too high motor current could be caused, for example, by a faulty cassette that does not allow the coupler to rotate properly. On the other hand, too low motor current could be caused, for example, by the emptying of the fluid from the system and the system needs to have the bag changed out.

The motor current limits differ for the different voltage levels selected by the up-down flow rate switch 109. In one embodiment, the desired ranges were set as follows:

(1) switch 198 set low, current range up to 1.95 A;
(2) switch 198 set medium, current range 1.04 A to 2.93 A; and
(3) switch 198 set high, current range 1.37 A to 3.91 A.

Although particular preferred embodiments of the invention have been disclosed in detail for illustrative purposes, it will be recognized that variations or modifications of the disclosed apparatus, including the rearrangement of parts, lie within the scope of the present invention.

What is claimed is:

1. A surgical irrigation apparatus, comprising:
an irrigation liquid handpiece for supplying irrigation liquid to a surgical site;
a fixedly supportable console including a rotatable drive coupler, said console having a front opening recess and forward tapered generally tubular shell extending forward in said front opening recess;
a cassette unit including (1) an irrigation liquid inlet tube, (2) a pump cassette connected to said irrigation liquid inlet tube in irrigation liquid receiving relation therewith and containing a bladed, rotatably driven, irrigation liquid engaging impeller, said pump cassette being nonrotatably received in said front opening recess and having a complimentarily forwardly tapered, rear opening chamber receiving said shell with said pump cassette received in said console recess, and (3) an irrigation liquid outlet tube in irrigation liquid supplying relation with said handpiece;
said rotatable drive coupler and said irrigation liquid impeller having horizontal axes, said pump cassette having a pre-use position pendant from said irrigation liquid inlet tube and spaced in front of said console with said horizontal axis of said rotatable drive coupler and said irrigation liquid impeller at least mutually adjacent, said pump cassette having a use position fixedly supported on and in front of said console with said console rotatable drive coupler and said pump cassette irrigation liquid impeller coupled in horizontally aligned driving relation, whereby to allow a surgical team member to simply push said pump cassette into its said use position on said console, in a rearward directed single movement, to provide availability of irrigation liquid for a given surgical procedure;
a latch mechanism cooperating between said pump cassette and said console recess, said pump cassette having a forward pump chamber separated by a substantially vertical wall from said rear opening chamber and containing said impeller, a generally horizontal rotatable shaft extending through said wall and fixedly carrying said impeller in said pump chamber and a driven coupler in said rear opening chamber, said couplers have generally horizontally extending and circumferentially interfingered sets of teeth, one said set being of resilient material, said inlet tube opening through a generally right angle path terminating in a generally horizontal inlet port into said pump chamber, said outlet tube being fed through an upward opening outlet port substantially at the vertical height of said shaft and of said inlet port and of a gravity filled level of said pump chamber;
wherein said pump cassette comprises a rear opening cassette body including said inlet and outlet ports and said rear opening chamber and a rear opening wiring chamber below said rear opening chamber, said pump cassette including a cassette cover assembly including a cup-like body received sealingly in a rear portion of said pump chamber and having a front end wall defining said substantially vertical wall, said cassette cover assembly having a substantially vertical flange extending radially outward at the rear end of said rear opening chamber and having a depending lower portion covering the rear of said wiring chamber, said console front opening recess having a rear wall and receiving said pump cassette flange closely adjacent said rear wall thereof, said flange depending lower portion having flexible electrical contacts protruding forward therefrom into said wiring chamber and rearward therefrom into flexible electric contact with opposing forward protruding contacts on said console recess rear wall, and a proximity sensing arrangement cooperating between said cassette body and said console recess.

2. The apparatus of claim 1, said irrigation liquid inlet port being substantially on said impeller horizontal axis and opening rearward toward said impeller, said irrigation liquid outlet port being elevated above the bottom portion of said pump chamber peripheral wall substantially to the height of said impeller horizontal axis, said pump chamber having a gravity fed, primed liquid level substantially at the height of said impeller axis.

3. The apparatus of claim 1 in which said console has (1) a motor operatively connected to said rotatable drive coupler, (2) an electric power supply, (3) a manually adjustable up/down flow rate, motor voltage setting switch and a pump primed detecting, motor current monitoring sensor, wherein motor current in a desired range corresponds to a primed condition of said pump cassette.

4. The apparatus of claim 1, wherein said proximity sensing arrangement comprises a magnet forward facing into said wiring chamber from said cassette body flange and closely opposing a magnet sensing switch rearward facing from said console recess rear wall, said apparatus including a battery and motor control circuitry in said console automatically enabled from said battery by said magnet sensing switch with said pump cassette in said use position on said console, a manually actuable motor-on switch on said handpiece having electric wires running into said pump cassette wiring chamber and fixed to the front of said resilient electrical contacts on said flange, said opposing contacts on said console recess rear wall being connected through said motor control circuitry for turning on said motor in response to actuation of said handpiece motor-on switch.

5. The apparatus of claim 4, wherein said console has a rear wall remote from said pump cassette and carrying (1) a clamp assembly for releasably and height adjustably fixing said console to an intermediate portion of a conventional upstanding irrigation liquid container support pole, (2) a power entry module and releasably engaging conventional AC power cord, and (3) a battery passage cover, said console having a rechargeable battery pack and a battery pack receiving passage opening rearward from said console and normally covered by said cover, said console housing a battery charger circuit energizable from said power cord for charging said battery pack.

6. The apparatus of claim 1, said latch mechanism having latch arms with free rearward portions extending rearward loosely through notches in the perimeter of said flange and latchingly engaging said console in said use position of said pump cassette on said console.

7. The apparatus of claim 6, wherein said wiring chamber is isolated from said pump chamber and said cup-like body.

8. The apparatus of claim 7 in which said handpiece includes a manually actuable switch, wires extending from said switch to said pump cassette and into said cassette body wiring chamber, the electrical contacts extending through said pump flange depending portion and connected to said wires in said wiring chamber and the contacts on said console comprising electrically engaging forward facing contacts, said contacts on said console being in circuit with a motor in said console, said motor having a substantially horizontal, forward facing, rotatable drive shaft extending through a forward wall of said console, said shaft having a forward end mounting and rotatably driving said rotatable drive coupler, said rotatable drive shaft being located substantially on the impeller horizontal axis with said pump cassette in the use position on said console.

9. In connection with a surgical irrigation apparatus, comprising:
an irrigation liquid handpiece for supplying irrigation liquid to a surgical site;
a fixedly supportable console including a motor having a rotatable drive coupler and an up-down flow rate switch;
a cassette unit including (1) an irrigation liquid inlet tube, (2) a pump cassette connected to said irrigation liquid inlet tube in irrigation liquid receiving relation therewith and having a rotatably driven irrigation liquid impeller, and (3) an irrigation liquid outlet tube in irrigation liquid supplying relation with said handpiece, in which said irrigation liquid impeller has a substantially horizontal rotation axis and in which said pump cassette has a pump chamber containing said irrigation liquid impeller and having a normal gravity fed irrigation liquid primed level substantially at said irrigation liquid impeller horizontal rotation axis, said handpiece having an irrigation liquid valve and a motor-on switch,
said cassette unit having a use position in which it is carried on said console with said rotatable drive coupler operatively connected to said irrigation liquid impeller and said motor in circuit with said motor-on switch, a method for assuring priming of said cassette unit installed on said console, comprising:
actuating said motor-on switch on said handpiece and applying a maximum voltage to said motor for a predetermined time duration T1;
sensing whether electric motor current is within a desired range;
if said motor current is within said range, running said motor at a first voltage level determined by an existing setting of said up-down flow rate switch;
if said motor current is above said desired range, noting that an error situation exists;
if said motor current is less than said desired range, then switching motor voltage low for a duration T2, thereafter applying said maximum voltage to said motor for another duration T1, and then again sensing whether said motor current is in said desired range; and
periodically rechecking motor current to determine if it is less than, greater than, or in said desired range, and if in the desired range, maintaining said motor at said first voltage level.

10. A surgical irrigation apparatus, comprising:
an irrigation liquid handpiece for supplying irrigation liquid to a surgical site;
a fixedly supportable console including a rotatable drive coupler, said console having a front wall, said console having a forward opening, non-circular pump cassette receiving recess in said console front wall, said console having a back wall and a peripheral wall extending forward from said back wall, said tapered portion of said console comprising a generally tubular shell extending forward from said recess back wall and loosely radially surrounded by said cassette receiving recess peripheral wall, said shell having a forward tapered outer peripheral face;
a cassette unit including (1) an irrigation liquid inlet tube, (2) a pump cassette connected to said irrigation liquid inlet tube in irrigation liquid receiving relation therewith and having a bladed rotatably driven, irrigation liquid engaging impeller, said pump cassette having a non-circular, outer periphery sized and shaped for rearward insertion in said cassette receiving recess, said pump cassette having a rear opening rear chamber bounded by a forward tapered peripheral wall, and (3) an irrigation liquid outlet tube in irrigation liquid supplying relation with said handpiece;

said console shell forward tapered outer peripheral face and said cassette chamber forward tapered peripheral wall defining releasably mating, complimentary, frusto-conical, horizontally extending, tapered portions on said horizontally opposed portions of said console and said pump cassette, said portions being respectively substantially coaxial with said rotatable drive coupler and said irrigation liquid impeller, said portions having a loosely telescoped pre-installed position, said portions having a snugly fixedly telescoped installed position in which said rotatable drive coupler and irrigation liquid impeller are fixedly located in substantially coaxial driving relation; and a resilient latch arm having (1) a front portion fixed on a front portion of said pump cassette outer peripheral wall, (2) a depressible intermediate portion extending rearward along said pump cassette, and (3) a rearward portion having a protruding finger, a slot in said cassette receiving recess of said console and receiving said finger in snap-fit relation, said finger having a front facing latch face trapped by said console with said finger full in said slot, said finger having a rear camming ramp cammingly engageable with said console with said finger partly entered in said slot, said latch arm depressible intermediate portion being engageable by the hand of a user for releasing said front facing latch face from said console slot.

11. The apparatus of claim 10 including complimentary releasable latch elements on said console and pump cassette and adjacent said tapered portions and which, in said installed position, fix said cassette unit on said console.

12. The apparatus of claim 10, wherein said resilient latch arm comprises a leaf spring-like resilient latch arm.

13. The apparatus of claim 10 in which said pump cassette has a rearward tapering cup-like portion and a forwardly disposed pump chamber separated by a substantially vertical wall, a rotatable shaft extending forward through said wall, said irrigation liquid impeller being rotatably located in said pump chamber and fixed with respect to said shaft, a driven coupler drivingly connected to said irrigation liquid impeller through said shaft and located in said cup-like portion, said driven coupler being complimentary to and drivingly engaged by said rotatable drive coupler of said console, said rearward opening cup-like portion defining one of said mating frustoconical tapered portions and snugly receiving said complimentary frustoconical tapered portion of said console, said console tapered portion being substantially tubular and in turn loosely housing said rotatable drive coupling and receiving said driven coupling.

14. A surgical irrigation apparatus, comprising:
an irrigation liquid handpiece for supplying irrigation liquid to a surgical site;
a fixedly supportable console including a rotatable drive coupler;
a cassette unit including (1) an irrigation liquid inlet tube, (2) a pump cassette connected to said irrigation liquid inlet tube in irrigation liquid receiving relation therewith and having a rotatably driven irrigation liquid engaging impeller, and (3) an irrigation liquid outlet tube in irrigation liquid supplying relation with said handpiece;
in which said pump cassette has a forward pump chamber with an upstanding rear wall, said irrigation liquid impeller being fixed on a rotatable shaft extending rearward through said wall, a driven coupler fixed on said rotatable shaft behind said rear wall and rotatably drivingly engaged by said rotatable drive coupler of said console, said rotatable drive coupler having forward extending drive teeth which are circumferentially spaced and circumferentially snugly received between corresponding rearward extending driven teeth of said driven coupler, the teeth of one of said couplers being of a rigid material and the teeth of the other one of said couplers being of resilient material tolerant of at least some misalignment between said couplers, said driven coupler comprising a disc-like base and a rearward extending driven coupler hub, said driven teeth being equally circumferentially spaced and extending rearward from said base and beyond said hub, said driven teeth extending radially outward from said hub substantially to the peripheral edge of said base, radially outer surfaces of said driven teeth being rearward extensions of said peripheral edge of said base, said driven teeth having circumferentially spaced sides lying in planes extending rearward and toward the longitudinal axis of said shaft and said hub at a first angle, the free rear ends of said driven teeth being pointed in profile looking radially inward as defined by rearwardly convergent planar ramp faces meeting at their rearward edges in a radially extending ridge line, said driven teeth each having a radially inboard face angled rearward and somewhat radially outward from the rear end of said hub at a second angle, said drive coupler having a drive coupler hub centered between said drive teeth, said drive teeth differing in size and shape from said driven teeth so as to be axially and circumferentially drivably received between said driven teeth, the circumferentially spaced sides of a given said drive tooth lying in planes converging toward said drive coupler hub at a third angle and meeting on an axial line through the rear portion of said hub and spaced radially outward from the central axis of said drive coupler hub, said third angle being wider than said first angle, the radially outer portion of a given said drive tooth fitting snugly circumferentially between the radially outer portions of two said driven teeth to transmit torque through the radially outer portions of said drive and driven teeth.

15. The apparatus of claim 14 in which said pump cassette comprises a cassette body from which said pump chamber opens rearward and a cassette cover having a rearward opening cup-like body snugly and sealingly received in said rearward opening cassette body, said cup-like body having a front end wall defining said upstanding rear wall of said pump chamber, said impeller being disposed forward of said cup-like body, said drive and driven couplers being disposed in said cup-like body, said cassette body having console engaging latch arms with springy free portions extending rearward past said rearward opening cup-like body and said couplers.

16. A surgical irrigation apparatus, comprising:
an irrigation liquid handpiece for supplying irrigation liquid to a surgical site;
a fixedly supportable console including a rotatable drive coupler;
a cassette unit including (1) an irrigation liquid inlet tube, (2) a pump cassette connected to said irrigation liquid inlet tube in irrigation liquid receiving relation therewith and having a rotatably driven irrigation liquid impeller, and (3) an irrigation liquid outlet tube in irrigation liquid supplying relation with said handpiece;

said console having an electrical circuit including an electric power source and an electric motor drivingly engaging said rotatable drive coupler, said handpiece having an irrigation liquid input from said pump cassette;

a pump control switch operably associated with said pump cassette, said console and pump cassette having horizontally opposed upstanding front and rear faces, respectively, console electric contacts on said console front face, pump cassette electric contacts on said pump cassette rear face each electrically engaging corresponding ones of said console electric contacts, said contacts of said console being in electric driving relation with said motor, said contacts of said pump cassette being in electrically connected relation with said pump control switch, a said contact of one of said console and said pump cassette being of resilient electrically conductive material and protruding toward and resiliently flexingly engaging a corresponding said contact protruding on the other of said console and said pump cassette, for reliable electric current conduction therebetween, wherein a given said resilient contact of resilient electrically conductive material has a profile and comprises a generally keyhole shaped central opening widened in the rear and narrowed in the front, said resilient contact having a relatively wide, convexly rounded, rear portion and tapering to a narrowed front portion, said resilient contact having oppositely facing outward opening grooves immediately behind said narrowed front portion thereof, and to the immediate rear of which lips angle forwardly and oppositely outwardly.

17. The apparatus of claim 16, wherein the profile of the given said contact of resilient electrically conductive material is a generally arrow-head profile.

18. The apparatus of claim 16, wherein said pump cassette includes a rearward opening cassette body and a cassette cover having a rearward opening cup-like body extending forwardly into a rear opening portion of said cassette body and defining therein a pump chamber ahead of said cup-like body and housing said impeller, said cassette cover further comprising a radially extending flange on the rear end of said rearward opening cup-like body thereof, said cassette body having a rear opening wiring chamber beside said pump chamber, said flange having a radially extended portion closing said wiring chamber and having forwardly extending, rearwardly opening, box-like bosses, said bosses having forward end walls including slots, the narrowed front portion of the given said resilient contact being inserted forwardly into said rear opening boss and snap-fitted through the corresponding said slot in said boss front wall, said slot having top and bottom edges received in said corresponding grooves in said given contact and retained therein to block rearward escape of said given resilient contact, said given resilient contact having lips disposed within said rearward opening boss and resiliently bearing against said boss front wall to block further movement of said resilient contact with respect to said boss end wall, said widened rear portion of said given resilient contact extending rearward slightly and being exposed adjacent the rear face of said flange to resiliently and electrically engage a protruding front head of the corresponding contact of said console, the narrow front portion of said resilient contact resiliently and electrically conductively pressing against a corresponding conductive terminal in said wiring chamber.

19. A surgical irrigation apparatus, comprising:

an irrigation liquid handpiece for supplying irrigation liquid to a surgical site, said handpiece including a manually actuatable handpiece switch;

a fixedly supportable console including a rotatable drive coupler;

a cassette unit including (1) an irrigation liquid inlet tube, (2) a pump cassette connected to said irrigation liquid inlet tube in irrigation liquid receiving relation therewith and having a rotatably driven irrigation liquid impeller, and (3) an irrigation liquid outlet tube in irrigation liquid supplying relation with said handpiece;

said pump cassette including a wiring chamber, a wire cable connected at a first end to the handpiece switch and extending from said handpiece into said wiring chamber of said pump cassette, a flange closing the rear end of said wiring chamber, contacts in said flange being wired to a second end of said wire cable, a magnet in said flange, said console having a front wall, said cassette unit having a use position mounted on said console with said flange closely adjacent said console front wall, a sensor in said console at said front wall and closely opposing said magnet with said pump cassette in said use position on said console, said console including an impeller drive motor, a battery and circuitry energizable by said battery in response to said activation of said sensor by said magnet and operably connected with said sensor such that installing said pump cassette in said use position on said console automatically energizes said circuitry from said battery, and including contacts on said console front wall in said use position of said pump cassette on said console engaging the contacts in said flange, said contacts on said console being operatively connected through said circuitry for energizing said motor upon manual actuation of said handpiece switch.

20. The apparatus of claim 19 in which the pump cassette comprises a cassette body having a rear opening pump chamber receiving said impeller and in liquid communication with said irrigation liquid inlet tube and said outlet tube, said pump cassette further including a cassette cover having a cup-like body including a front wall closing the rear of said pump chamber, said flange extending radially from the rear portion of said cup-like body, said wiring chamber opening rearward from said cassette body and located beside and separated from said pump chamber and cup-like body, said flange extending from said cup-like body and closing the rear of said wiring chamber.

21. A surgical irrigation apparatus, comprising:

an irrigation liquid handpiece for supplying irrigation liquid to a surgical site, said handpiece including a handpiece switch;

a fixedly supportable console including a rotatable drive coupler;

a cassette unit including (1) an irrigation liquid inlet tube, (2) a cassette connected to said irrigation liquid inlet tube in irrigation liquid receiving relation therewith and having a rotatably driven irrigation liquid impeller, and (3) an irrigation liquid outlet tube in irrigation liquid supplying relation with said handpiece;

said console having an electrical circuit including an electric power source and an electric motor drivingly engaging said rotatable drive coupler, said handpiece having an irrigation liquid input to receive irrigation liquid from said cassette through said liquid outlet tube; and said console and said cassette having horizontally opposed upstanding front and rear faces, respectively, console electric contacts on said console front face, and cassette electric contacts on said cassette rear face for electrically engaging corresponding ones of said console electric contacts, said console electric contacts being in electric driving relation with said motor, said contacts of said cassette being in electrically connected relation with said handpiece switch via a wire cable connected at a first end to said handpiece switch and at a second end to said contacts of said cassette, a said contact of one of said console and said cassette being of resilient electrically conductive material and protruding toward and resiliently flexingly engaging a corresponding said contact protruding on the other of said console and said cassette, wherein actuating said handpiece switch provides a current path through said wire cable, said cassette electric contacts, and said console electric contacts to said motor for driving said irrigation liquid impeller to supply irrigation liquid through the handpiece to a surgical site.

* * * * *